US010864234B2

(12) United States Patent
Tuan

(10) Patent No.: US 10,864,234 B2
(45) Date of Patent: Dec. 15, 2020

(54) STEM CELL-BASED TECHNOLOGIES FOR AVIAN SKELETAL TISSUE ENGINEERING AND REGENERATION

(71) Applicant: University of Pittsburgh—Of the Commonwealth System of Higher Education, Pittsburgh, PA (US)

(72) Inventor: Rocky S. Tuan, Pittsburgh, PA (US)

(73) Assignee: University of Pittsburgh—Of the Commonwealth System of Higher Education, Pittsburgh, PA (US)

( * ) Notice: Subject to any disclaimer, the term of this patent is extended or adjusted under 35 U.S.C. 154(b) by 66 days.

(21) Appl. No.: 15/525,570

(22) PCT Filed: Nov. 4, 2015

(86) PCT No.: PCT/US2015/059005
§ 371 (c)(1),
(2) Date: May 9, 2017

(87) PCT Pub. No.: WO2016/077118
PCT Pub. Date: May 19, 2016

(65) Prior Publication Data
US 2017/0333488 A1 Nov. 23, 2017

Related U.S. Application Data

(60) Provisional application No. 62/077,764, filed on Nov. 10, 2014.

(51) Int. Cl.
*A61K 35/57* (2015.01)
*A61L 27/22* (2006.01)
*A61L 27/38* (2006.01)
*A61L 27/52* (2006.01)
*A61K 47/32* (2006.01)
*A61K 47/42* (2017.01)
*A61K 9/06* (2006.01)
*A61L 27/16* (2006.01)

(52) U.S. Cl.
CPC ............. *A61K 35/57* (2013.01); *A61K 9/06* (2013.01); *A61K 47/32* (2013.01); *A61K 47/42* (2013.01); *A61L 27/16* (2013.01); *A61L 27/222* (2013.01); *A61L 27/3834* (2013.01); *A61L 27/3847* (2013.01); *A61L 27/3852* (2013.01); *A61L 27/52* (2013.01); *A61L 2300/64* (2013.01); *A61L 2430/02* (2013.01); *A61L 2430/06* (2013.01)

(58) Field of Classification Search
None
See application file for complete search history.

(56) References Cited

U.S. PATENT DOCUMENTS

| 7,235,592 B2 * | 6/2007 | Muratoglu | C08J 3/28 |
| | | | 522/150 |
| 2005/0069572 A1 | 3/2005 | Williams et al. | |
| 2011/0177132 A1 | 7/2011 | Allon et al. | |
| 2016/0129155 A1 | 5/2016 | Lin et al. | |

FOREIGN PATENT DOCUMENTS

| EP | 1673440 A2 | 6/2006 |
| EP | 2120971 A1 | 11/2009 |
| WO | WO 2000/029552 | 5/2000 |
| WO | WO 2009/006558 | 1/2009 |
| WO | WO 2010/074958 A1 | 7/2010 |
| WO | WO 2012/058617 | 5/2012 |

OTHER PUBLICATIONS

Oryan et al. Role of mesenchymal stem cells in bone regenerative medicine: what is the evidence? Cells Tissues Organs. 2017;204:59-83.*
Morrow et al. Fetal skull trauma in caged layer chickens associated with a moving feed hopper: diagnosis based on autopsy examination, forensic computed tomography and farm visit. Avian Pathology. 2012;41(4):391-394.*
"Fundamentals of Mercury Arc Lamps," http://zeiss-campus.magnet.fsu.edu/articles/lightsources/mercuryarc.html, accessed Jul. 17, 2017.
Gottardi et at, "An Osteochondral Microphysiological System to Study the Pathogenesis of Osteoarthritis and the Effect of Hormonal Exposure," *Department of Orthopaedic Surgery*, 1 page (2014).
Hui et al., "In Vitro Chondrogenic Differentiation of Human Mesenchymal Stem Cells in Collagen Microspheres: Influence of Cell Seeding Density and Collagen Concentration," *Biomaterials* 29:3201-3212 (Apr. 1, 2008).
Lin et al., "BMP-2 Gene Cell-functionalized 3D Scaffolds for the Repair of Cranial Bone Defect," *Center for Cellular and Molecular Engineering*, 2 pages (date unknown).
Lin et al., "Efficient Bone Formation ex vivo in Constructs of BMP2-transduced Human MSCs Encapsulated in Gelatin Scaffold Fabricated by Projection Stereolithography," *ORS 2014 Annual Meeting*, Poster No. 1532, 2 pages (2014).

(Continued)

Primary Examiner — Robert M Kelly
(74) Attorney, Agent, or Firm — Klarquist Sparkman, LLP

(57) ABSTRACT

Methods are disclosed for forming bone and/or cartilage in an avian subject. The methods include administering to the avian subject a therapeutically effective amount of a composition comprising avian mesenchymal stem cells and a hydrogel that supports the differentiation of the avian mesenchymal stem cells into cells of an osteogenic and/or condrogenic lineage. In some embodiments, methods are disclosed for repairing a bone defect and preventing infection, such as that associated bone fracture, in an avian subject. The methods include administering locally to the bone defect a composition comprising a therapeutically effective amount of avian mesenchymal stem cells and a hydrogel, such as a methacrylated gelatin hydrogel.

21 Claims, 13 Drawing Sheets

(56) References Cited

OTHER PUBLICATIONS

Lin et al., "Medical Imaging-guided Fabrication of Human Osteochondral issues using Projection Stereolithography (PSL)," *Center for Cellular and Molecular Engineering*, 2 pages (date unknown).
Lin et al., "Projection Stereolithographic Fabrication of bone Scaffold Encapsulated with Lenti-BMP-2 transduced human Bone Marrow Stem Cells (hBMSCs)," Posterboard (2013).
Lin et al., "Stem Cell-Based Microphysiological Osteochondral System to Model Tissue Response to Interleukin-1β," *Molecular Pharmaceutics* 11:2203-2212 (May 15, 2014).
Lin et al., "Fabrication of 3-Dimensional Live Cell-Biomaterial Constructs Using a Visible Light-Based Dimensional Live Cell-Biomaterial Constructs using a Visible Light-Based Stereolithographic Printer," Abstract and podium presentation in *Orthopaedic Research Society* (ORS) 2012 Annual Meeting, San Francisco, CA, 1 page (Feb. 4, 2012).
Lin et al., "Single-Step Projection Stereolithographic Fabrication of Gene-Activated Bone Scaffold Encapsulating Human Bone Marrow Stem Cells and Lenti-BMP-2 Viral Vector," Abstract and NIRA finalists' presentation in *Orthopaedic Research Society* (ORS) 2013 Annual Meeting, San Antonio, TX, 3 pages (Jan. 22, 2013).
Lin, "Repair of Osteochondral Defect Using Photocrosslinked Gelatin/Hyaluronic Acid Scaffold," *Center for Cellular and Molecular Engineering*, 2 pages (Dec. 2014).
Nichol et al., "Cell-laden Microengineered Gelatin Methacrylate Hydrogels," *Biomaterials* 31:5536-5544 (Mar. 25, 2010).
Sun et al., "Projection Stereolithographic Fabrication of Human Adipose Stem Cell-incorporated Biodegradable Scaffolds for Cartilage tissue Engineering," *Frontiers*, 20 pages (date unknown).
Krasnodembskaya et al., "Antibacterial effect of human mesenchymal stem cells is mediated in part from secretion of the antimicrobial peptide LL-37," *Stem Cells* 28(12): 2229-2238 (Dec. 1, 2010).
Bai et al., "Biological characterization of chicken mesenchymal stem/progenitor cells from umbilical cord Wharton's Jelly," *Molecular and Cellular Biochemistry* 376: 95-102 (2013).
Gao et al., "Isolation and characterization of chicken dermis-derived mesenchymal stem/progenitor cells," *BioMed Research International* 2013: Article ID: 626258, 8 pages (Epub Aug. 4, 2013).

International Search Report from parent PCT Application No. PCT/US2015/059005, 5 pages (dated Dec. 9, 2015).
Kocamaz et al., "Implication of C-type natriuretic peptide-3 signaling in glycosaminoglycan synthesis and chondrocyte hypertrophy during TGF-β1 induced chondrogenic differentiation of chicken bone marrow-derived mesenchymal stem cells," *Journal of Molecular Histology* 43: 497-508 (2013).
Lin et al., "Application of visible light-based projection stereolithography for live cell-scaffold fabrication with designed architecture," *Biomaterials* 34: 331-339 (2013).
Lin et al., "Cartilage tissue engineering application of injectable gelatin hydrogel with in situ visible-light-activated gelation capability in both air and aqueous solution," *Tissue Engineering Part A* 20(17-18): 2402-2411 (Epub Apr. 9, 2014).
Martin et al., "In vitro differentiation of chick embryo bone marrow stromal cells into cartilaginous and bone-like tissues." *Journal of Orthopaedic Research* 16(2): 181-189 (Mar. 1, 1998).
Smith et al., "Evaluation of skeletal tissue repair, part 1: Assessment of novel growth-factor-releasing hydrogels in an ex vivo chick femur defect model," *Acta Biomaterialia* 10(10): 4186-4196 (Epub Jun. 14, 2016).
Written Opinion from parent PCT Application No. PCT/US2015/059005, 6 pages (dated Dec. 9, 2015).
Zheng et al., "Chondrogenic differentiation of mesenchymal stem cells induced by collagen-based hydrogel: An in vivo study," *Journal of Biomedical Materials Research Part A* 93A(2): 783-792 (May 1, 2010). (Abstract only).
Hoffman, "Hydrogels for biomedical applications," *Advanced Drug Delivery Reviews* 64: 18-23 (2012).
Sittipon Intarapat and Stern "Chick stem cells: Current progress and future prospects," *Stem Cell Research* 11: 1378-1392 (2013).
Kahn and Simmons, "Investigation of cell lineage in bone using a chimaera of chick and quail embryonic cells," *Nature* 258: 325-327 (Nov. 27, 1975).
Le Douarin et al., "Chapter 2. Quail-chick transplantations," *Methods in Cell Biology* 51: 23-59 (1996).
Li et al., "Differentiation potential of bone marrow mesenchymal stem cells in duck," *Journal of Genetics and Genomics* 36: 133-140 (2009).

* cited by examiner

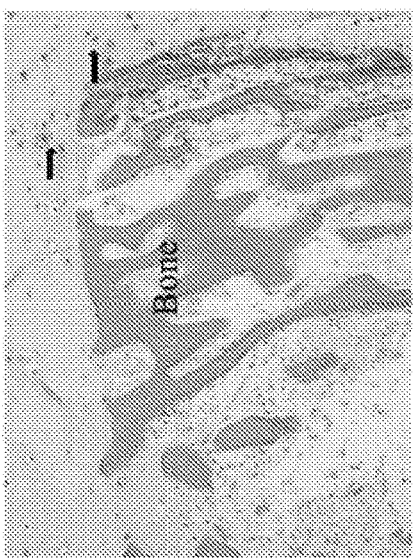
FIG. 11A Cell-free construct
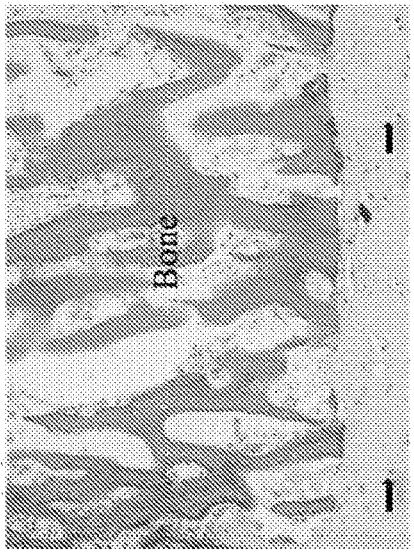
FIG. 11B Pre-osteo naïve MSC-seeded
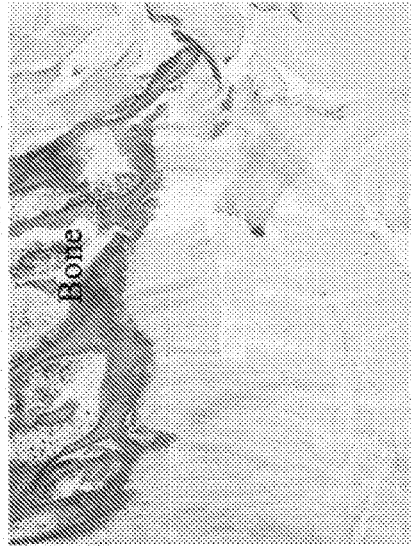
FIG. 11C Osteo-MSC-seeded
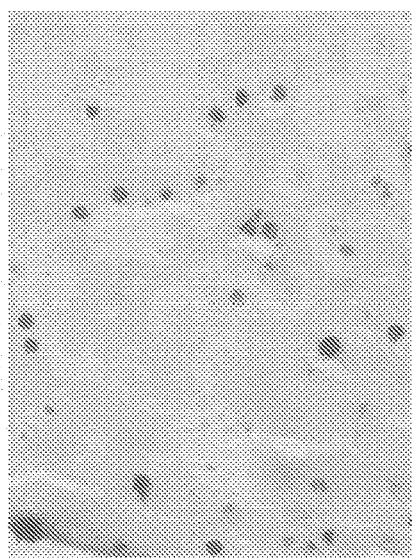
FIG. 11D Osteocalcin immunostaining: Native bone
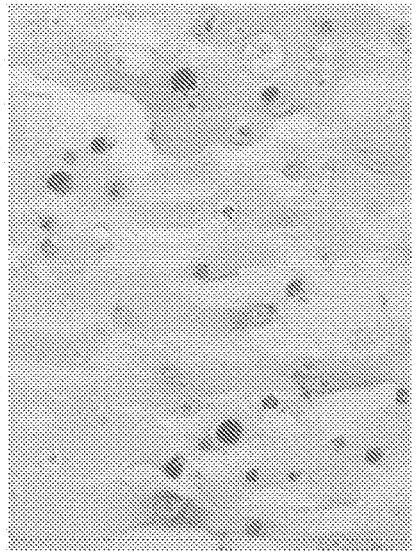
FIG. 11E Osteocalcin immunostaining: Pre-osteo naïve MSC-seeded
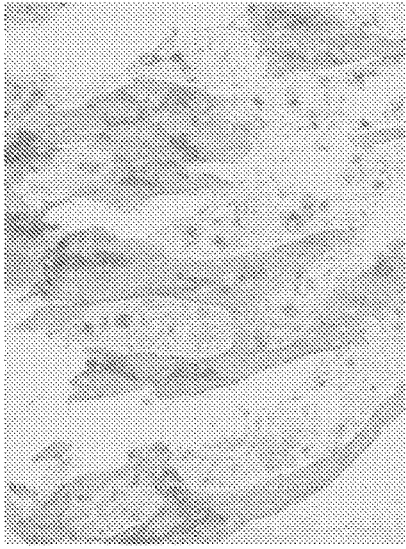
FIG. 11F Osteocalcin immunostaining: Osteo-MSC-seeded

Anti-Bacterial Effects of Bone Marrow-Derived MSCs

Chick Bone Marrow MSCs

Human Bone Marrow MSCs

US 10,864,234 B2

STEM CELL-BASED TECHNOLOGIES FOR AVIAN SKELETAL TISSUE ENGINEERING AND REGENERATION

CROSS REFERENCE TO RELATED APPLICATION

This is a § 371 U.S. national stage of International Application No. PCT/US2015/059005, filed Nov. 4, 2017, which was published in English under PCT Article 21(2), which This claims the benefit of U.S. Provisional Application No. 62/077,764, filed Nov. 10, 2014, which is incorporated by reference herein in its entirety.

FIELD

This relates to the field of skeletal diseases, specifically to the use of a hydrogel and avian mesenchymal stem cells (MSCs) for engineering and regenerating skeletal tissues, including bone and cartilage, and for the treatment of bone infection, such as osteomyelitis in birds.

BACKGROUND

Skeletal pathologies are common to all vertebrate animals, particularly those affecting limbs, due to genetic, developmental, metabolic, or injurious causes. Avian animals are no exception, including species that are domesticated, such as exotic or fancy birds and birds of prey, or kept for agricultural purposes. For abnormalities affecting the limbs, specifically the wings or legs, there has been little to no new clinical treatments for the last many decades.

Avian bones have a high calcium content compared with bones of mammals and have a large medullary canal. They are often described as thin and brittle, and are prone to shattering upon impact. Many bones (such as the humerus and femur) are pneumatic and involved in respiration and humidification of air. The soft tissues are not strongly adhered to bones in the distal extremities. These factors contribute to the high incidence of open, comminuted fractures and make iatrogenic fracture during repair attempts a significant concern. There also are congenital, genetic, and metabolic skeletal pathologies of birds, including those that affect the growth plate of long bones (e.g., dyschondroplasia and chondrodystrophy), those that affect the structure and function of the joint articular cartilage (e.g., chondrosis), as well as osteoporosis and osteopenia.

With regard to fractures, it has been demonstrated that autogenous bone grafts are beneficial in avian fracture management. As noted above, the humerus and femur are pneumatic, and thus are not sources of cancellous bone. Furthermore, the distal bones of the extremities are often small and narrow making them poor donor sites. In large birds and terrestrial birds, the tibiotarsus may provide adequate cancellous bone for grafting. Thus, the corticocancellous grafts are often used, as onlay grafting or the bone cut into fragments and used around the fracture site or packed into cortical defects. However, the process is complex (for review, see Bennett et al., "Avian Orthopedics," available on-line at c.ymcdn.com/sites/www.michvma.org/resource/resmgr/mvc_proceedings_2014/bennett_03.pdf).

Another complication associated with fractures in birds is osteomyelitis, a painful inflammatory disease of bone caused by bacterial infection. Although the feathery and scalar nature of avian skin represents a generally effective barrier, injuries such as open fractures with accompanying skin rupture lead to bacterial entry into the injury site that can result in bone infection and hematogenous infection in other tissues. Early and effective prevention and/or control of the infection is thus critical.

There is thus a need for materials and cells that can be used for skeletal repair and treatment of skeletal pathologies in birds.

SUMMARY

Avian bones are different from mammalian bones, and birds are prone to developing osteomyelitis. There is a need for methods for forming bone in avian subjects, and for treating osteomyelitis.

Methods are disclosed for forming bone and/or cartilage in an avian subject. The methods include administering to the avian subject a therapeutically effective amount of a composition comprising avian mesenchymal stem cells and a hydrogel that supports the differentiation of the avian mesenchymal stem cells into cells of an osteogenic and/or chondrogenic lineage, thereby forming bone and/or cartilage in the avian subject. In some embodiments, the methods utilize a photocrossslinkable hydrogel, such as a biocompatible gelatin and/or hyaluronan hydrogel. In some non-limiting examples, the hydrogel is methacrylated gelatin and/or methacrylated hylauronan.

In some embodiments, methods are disclosed for repairing a bone defect in an avian subject. The methods include administering locally to the bone defect a composition comprising a therapeutically effective amount of avian mesenchymal stein cells and hydrogel, such as a hydrogel that can be photocrosslinked with visible or ultraviolet (UV) light, thereby repairing the bone defect. In some non-limiting examples, the hydrogel is methacrylated gelatin and/or methacrylated hyaluronan.

In additional embodiments, methods are provided for treating bone infection, such as, but not limited to, osteomyelitis. The methods include administering locally to the bone infection a composition comprising a therapeutically effective amount of avian mesenchymal stem cells and hydrogel, such as a hydrogel that can be photocrosslinked with visible or ultraviolet (UV) light, thereby treating the infection. In some non-limiting examples, the hydrogel is methacrylated gelatin and/or methacrylated hyaluronan.

The foregoing and other objects, features, and advantages of the invention will become more apparent from the following detailed description, which proceeds with reference to the accompanying figures.

BRIEF DESCRIPTION OF THE DRAWINGS

(FIG. 1A) 24 hours after initial plating, showing cell colony formation. (FIG. 1B) Four-day culture, showing proliferation of the attached cells. (FIG. 1C) Three days after the first passage, showing proliferation and the appearance of slender, spindle shaped cells, consistent with MSC phenotype.

(FIG. 2A) Osteogenesis: (top) phase contrast view showing the accumulation of conspicuous matrix mineralization; (bottom) alizarin red staining confirmation matrix calcification. (FIG. 2B) Chondrogenesis: (top) phase contrast view showing formation of matrix-rich nodules; (bottom) Alcian blue staining revealing proteoglycan-rich matrix, characteristic of cartilage matrix. (FIG. 2C) Adipogenesis: (top) phase contrast view showing appearance of refractile cytoplasmic accumulation of lipid droplets; (bottom) Oil Red O staining confirming the presence of intracellular lipid accumulation. (FIG. 2D) Control culture: (top) MSCs proliferated extensively, shown by phase contrast microscopy; (bottom) lack of matrix formation or lipid accumulation, as seen after Oil Red O staining.

(FIG. 5A) Chick sternum views showing location of the surgical defect site (cored cylinder and circle). (FIG. 5B) Chick skull illustrating the location of the calvarial bone (box), and the site of surgical defect (circle) to be implanted with MSC-hydrogel construct.

(FIG. 8A) MSC-seeded implant. MSCs implanted in a photocrosslinked gelatin hydrogel into the defect site produce abundant cartilaginous matrix (Safranin O-stained, red) (arrow), particularly those immediately adjacent to the host sternum (asterisk) where integration between host and implant matrix is apparent. It is noteworthy that most of the gelatin hydrogel (blue stain) has been resorbed, suggesting matrix remodeling by the implanted MSCs. (FIG. 8B) Cell-free implant. The gelatin implant remains mostly intact (stained blue) after culture, with total absence of Safranin O-positive matrix, as well as the absence of integration with the host sternum matrix.

(FIG. 9A) MSC-seeded implant. (Top) Alizarin Red staining. MSCs implanted in a photocrosslinked gelatin hydrogel into the calvaria defect site produce abundant calcified matrix (Alizarin Red stained) (arrow), including those immediately adjacent to the host sternum (asterisk). The mineralized matrix of the host tissue appears integrated with that of the cells in the implant. (Bottom) Hematoxylin-eosin staining. (FIG. 9B) Cell-free implant. (Top) Alizarin Red staining. The gelatin implant remains unmineralized after culture, with total absence of Alizarin Red-positive matrix. Occasional void space appears, mostly resulting from bubbles in the original gel mixture. (Bottom) Hematoxylin-eosin staining, showing absence of cells in the gelatin scaffold.

FIG. 10. Macroscopic appearance of ex vivo bone fracture repair using MSCs. The three groups of tibia-MSC composite cultures were viewed after four weeks of ex vivo culture. Substantial opacity was seen in the MSC seeded cultures; naïve MSCs and pre-osteogenically differentiated MSCs appeared similar.

FIG. 11A-11F. Histological analysis of ex vivo fracture repair using MSC-seeded implants. Histological examination of the fracture repair site was done by (FIG. 11A-11C) hematoxylin-eosin staining, and (FIG. 11D-i IF) by immunohistochemical staining for osteocalcin, a bone matrix-specific protein. (FIG. 11A-11C) Abundant cells are present only in the cell-seeded implanted constructs (FIG. 11B and FIG. 11C), indicated by arrows, adjacent to the host matrix-rich trabecular bone (Bone). (FIG. 11D-11F) Ostocalcin immunostaining is specific for bone matrix, as seen in the native trabecular bone (FIG. 11D). Similar staining is seen in the MSC-seeded implants (FIG. 11E and FIG. 11F). MSCs appeared to perform equally with or without pre-osteogenic differentiation in vitro, presumably because after implantation, they were residing in a naturally osteogenic environment.

DETAILED DESCRIPTION

Figure 1A:
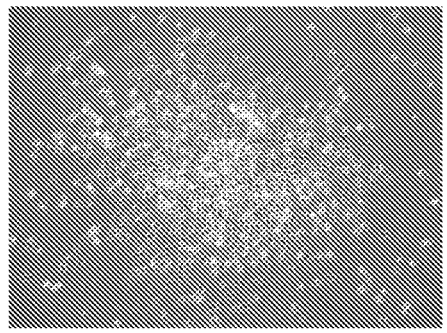
FIGS. 1A-1C. Morphology of primary cultures of chick bone marrow mesenchymal stem cells (MSCs) (phase contrast microscopy).

Disclosed herein are three dimensional photo cosslinked hydrogels that include avian mesenchymal stem cells. These hydrogels can be used to form bone and/or cartilage in an avian subject. In some embodiments the hydrogels are of use for bone and cartilage repair, and are of use for the treatment of a fracture or osteomyelitis. In specific non-limiting examples, the hydrogel can be a methacrylated gelatin hydrogel. These hydrogels can be crosslinked with visible light.

In some embodiments, a therapeutically effective amount of a composition is introduced into an avian subject, wherein the composition includes avian mesenchymal stem cells and a matrix, such as three dimensional photocrosslinked hydrogel that supports the differentiation of the avian mesenchymal stem cells into cells of an osteogenic and/or condrogenic lineage.

Terms

Unless otherwise noted, technical terms are used according to conventional usage. Definitions of common terms in molecular biology may be found in Benjamin Lewin, *Genes V*, published by Oxford University Press, 1994 (ISBN 0-19-854287-9); Kendrew et al. (eds.), *The Encyclopedia of Molecular Biology*, published by Blackwell Science Ltd., 1994 (ISBN 0-632-02182-9); and Robert A. Meyers (ed.), *Molecular Biology and Biotechnology: a Comprehensive Desk Reference*, published by VCH Publishers, Inc., 1995 (ISBN 1-56081-569-8).

In order to facilitate review of the various embodiments of this disclosure, the following explanations of specific terms are provided:

Administration: The introduction of a composition into a subject by a chosen route. The route can be local or systemic. For example, if the chosen route is intravenous, the composition is administered by introducing the composition into a vein of the subject. If the chosen route is local, such as for treatment of fracture, the composition can be administered by introducing the composition into the tissue gap in the fracture site.

Amplification: A technique that increases the number of copies of a nucleic acid molecule (such as an RNA or DNA). An example of amplification is polymerase chain reaction (PCR), in which a sample is contacted with a pair of oligonucleotide primers under conditions that allow for the hybridization of the primers to a nucleic acid template in the sample. The primers are extended under suitable conditions, dissociated from the template, re-annealed, extended, and dissociated to amplify the number of copies of the nucleic acid. The product of amplification can be characterized by electrophoresis, restriction endonuclease cleavage patterns, oligonucleotide hybridization or ligation, and/or nucleic acid sequencing using standard techniques. The reaction product can be quantified. Reverse transcription PCR (RT-PCR) is a technique wherein RNA is reverse transcribed into cDNA and amplified.

Other examples of amplification include quantitative real-time polymerase chain reaction (qPCR), strand displacement amplification, as disclosed in U.S. Pat. No. 5,744,311; transcription-free isothermal amplification, as disclosed in U.S. Pat. No. 6,033,881; repair chain reaction amplification, as disclosed in PCT publication WO 90/01069; ligase chain reaction amplification, as disclosed in European patent publication EP-A-320,308; gap filling ligase chain reaction amplification, as disclosed in U.S. Pat. No. 5,427,930; and NASBA RNA transcription-free amplification, as disclosed in U.S. Pat. No. 6,025,134. Several embodiments include multiplex qPCR assays, which are useful for amplifying and detecting multiple nucleic acid sequences in a single reaction.

Biocompatible: Any material, that, when implanted in an avian subject, does not provoke an adverse response in the bird. A biocompatible material, when introduced into an individual, is not toxic or injurious to that individual, nor does it induce immunological rejection of the material in the subject.

Bone defect: Includes any disease, defect, or disorder which affects bone strength, function, and/or integrity, such as those resulting from injury, or a defect brought about during the course of surgery, infection, malignancy, or developmental malformation. Examples of bone defects include, but are not limited to, fractures (such as a critical defect or non-union fracture), dental or facial defects (such as cleft palate or facial, skull, or dental injuries or malformations). Other examples of bone defects include damage to bones resulting from diseases of bone fragility, such as osteoporosis, and malignancies and/or cancers of the bone such as a sarcoma, such as osteosarcoma.

Bone disease: Includes any disease or disorder which affects bone strength, function, and/or integrity, such as decreasing bone tensile strength and modulus. Examples of bone diseases include, but are not limited to, diseases of bone fragility and genetic diseases which result in abnormal bone formation. Bone diseases include, but are not limited to, osteogenesis imperfecta, osteoporosis, or a metabolic bone disease. Other examples of bone diseases include malignancies and/or cancers of the bone such as a sarcoma, such as osteosarcoma.

Bone-forming cells and mineral forming cells: Cells having osteogenic potential. Examples include, but are not limited to: bone marrow stromal cells, adipose-derived stem cells, osteoblasts, osteocytes, and dental pulp cells. "Osteogenesis" is the formation or production of bone.

Bone Healing and Fracture Healing: Bone heals (fuses) in a unique way compared with other connective tissues. Rather than develop scar tissue, it has the innate ability to regenerate itself completely. The majority of fractures heal by secondary fracture healing, that involves a combination of intramembranous and endochondral ossification. Without being bound by theory, it is generally believed that the fracture healing sequence involves five discrete stages of healing. This includes an initial stage in which a hematoma is formed and inflammation occurs; a subsequent stage in which cartilage begins to form and angiogenesis proceeds, and then three successive stages of cartilage calcification, cartilage resorption and bone deposition, and ultimately a more chronic stage of bone remodeling. Generally, committed osteoprogenitor cells and uncommitted, undifferentiated mesenchymal cells contribute to the process of fracture healing. Bone that forms by intramembranous ossification is found early and further from the site of the fracture, results in the formation of a hard callus, and forms bone directly without first forming cartilage. Generally, two weeks after fracture, cell proliferation declines and hypertrophic chondrocytes become the dominant cell type in the chondroid callus, and undergo further matrix mineralization, followed by infiltration of bone-forming cells. The resulting endochondral bone is formed adjacent to the fracture site.

Bone Morphogenetic Proteins (BMPs): A family of proteins, identified originally in extracts of demineralized bone that were capable of inducing bone formation at ectopic sites. BMPs are found in minute amounts in bone material (approximately 1 microgram/kg dry weight of bone). Most members of this family (with the exception of BMP-1) belong to the transforming growth factor-β family of proteins.

BMPs can be isolated from demineralized bones and osteosarcoma cells. They have been shown also to be expressed in a variety of epithelial and mesenchymal tissues in the embryo. BMPs are proteins which act to induce the differentiation of mesenchymal-type cells into chondrocytes and/or osteoblasts before initiating bone formation. They promote the differentiation of cartilage- and bone-forming cells near sites of fractures but also at ectopic locations. Some of the BMPs induce the synthesis of alkaline phosphatase and collagen in osteoblasts. Some BMPs act directly on osteoblasts and promote their maturation while at the same time suppressing myogenic differentiation. Other BMPs promote the conversion of mesenchymal cells into chondrocytes, and are also capable of inducing the expression of an osteoblast phenotype in non-osteogenic cell types. Among the BMPs, BMP-2 and BMP-4 and BMP-7 have been shown to promote bone formation.

Bromodeoxyuridine (BrdU) incorporation: Brdu is a synthetic nucleoside analog, 5-bromo-2'-deoxyuridine. BrdU is commonly used in the detection of proliferating cells in living tissues. BrdU can be incorporated into the newly synthesized DNA of replicating cells during the S phase of the cell cycle. BrdU substitutes for thymidine during DNA replication, and thus can be used as an indication of cells that were actively replicating their DNA.

cDNA (complementary DNA): A piece of DNA lacking internal, non-coding segments (introns) and regulatory sequences that determine transcription. cDNA is synthesized in the laboratory by reverse transcription from messenger RNA extracted from cells. cDNA can also contain untranslated regions (UTRs) that are responsible for translational control in the corresponding RNA molecule.

Conservative Substitutions: Modifications of a polypeptide that involve the substitution of one or more amino acids for amino acids having similar biochemical properties that do not result in change or loss of a biological or biochemical function of the polypeptide are designated "conservative" substitutions. These conservative substitutions are likely to have minimal impact on the activity of the resultant protein. Table 1 shows amino acids that can be substituted for an original amino acid in a protein, and which are regarded as conservative substitutions.

TABLE 1

| Original Residue | Conservative Substitutions |
|---|---|
| Ala | ser |
| Arg | lys |
| Asn | gln; his |
| Asp | glu |
| Cys | ser |
| Gln | asn |
| Glu | asp |
| Gly | pro |
| His | asn; gln |
| Ile | leu; val |
| Leu | ile; val |
| Lys | arg; gln; glu |
| Met | leu; ile |
| Phe | met; leu; tyr |
| Ser | thr |
| Thr | ser |
| Trp | tyr |
| Tyr | trp; phe |
| Val | ile; leu |

One or more conservative changes, or up to ten conservative changes (such as two substituted amino acids, three substituted amino acids, four substituted amino acids, or five substituted amino acids, etc.) can be made in the polypeptide without changing a biochemical function of the osteogenic growth factor, such as a BMP, Cox-2, LIM-1 or FGF-2.

Contacting: Placement in direct physical association. Includes both in solid and liquid form.

Cross-linked: A composition containing intermolecular cross-links and optionally intramolecular cross-links, arising from the formation of covalent bonds. Covalent bonding between two cross-linkable components may be direct, in which case an atom in one component is directly bound to an atom in the other component, or it may be indirect, through a linking group. A cross-linked gel or polymer matrix may, in addition to covalent bonds, also include intermolecular and/or intramolecular noncovalent bonds such as hydrogen bonds and electrostatic (ionic) bonds. The term "cross-linkable" refers to a component or compound that is capable of undergoing reaction to form a cross-linked composition.

Cytokine: The term "cytokine" is used as a generic name for a diverse group of soluble proteins and peptides that act as humoral regulators at nano- to picomolar concentrations and which, either under normal or pathological conditions, modulate the functional activities of individual cells and tissues. These proteins also mediate interactions between cells directly and regulate processes taking place in the extracellular environment. Examples of cytokines include, but are not limited to, tumor necrosis factor-α, interleukin (IL)-6, IL-10, IL-12, transforming growth factor, and interferon-γ.

Degenerate variant: A polynucleotide encoding a, polypeptide, such as a PDGF polypeptide, that includes a sequence that is degenerate as a result of the genetic code. There are 20 natural amino acids, most of which are specified by more than one codon. Therefore, all degenerate nucleotide sequences are included as long as the amino acid sequence of the polypeptide encoded by the nucleotide sequence is unchanged.

DNA (deoxyribonucleic acid): DNA is a long chain polymer which comprises the genetic material of most living organisms (some viruses have genes comprising ribonucleic acid (RNA)). The repeating units in DNA polymers are four different nucleotides, each of which comprises one of the four bases, adenine (A), guanine (G), cytosine (C), and thymine (T) bound to a deoxyribose sugar to which a phosphate group is attached. Triplets of nucleotides (referred to as codons) code for each amino acid in a polypeptide, or for a stop signal. The term codon is also used for the corresponding (and complementary) sequences of three nucleotides in the mRNA into which the DNA sequence is transcribed.

Unless otherwise specified, any reference to a DNA molecule is intended to include the reverse complement of that DNA molecule. Except where single-strandedness is required by the text herein, DNA molecules, though written to depict only a single strand, encompass both strands of a double-stranded DNA molecule. Thus, a reference to the nucleic acid molecule that encodes a specific protein, or a fragment thereof, encompasses both the sense strand and its reverse complement. For instance, it is appropriate to generate probes or primers from the reverse complement sequence of the disclosed nucleic acid molecules.

Expressed: The translation of a nucleic acid sequence into a protein. Proteins may be expressed and remain intracellular, become a component of the cell surface membrane, or be secreted into the extracellular matrix or medium.

Expression Control Sequences: Nucleic acid sequences that regulate the expression of a heterologous nucleic acid sequence to which it is operatively linked. Expression control sequences are operatively linked to a nucleic acid sequence when the expression control sequences control and regulate the transcription and, as appropriate, translation of the nucleic acid sequence. Thus expression control sequences can include appropriate promoters, enhancers, transcription terminators, a start codon (ATG) in front of a protein-encoding gene, splicing signal for introns, maintenance of the correct reading frame of that gene to permit proper translation of mRNA, and stop codons. The term "control sequences" is intended to include, at a minimum, components whose presence can influence expression, and can also include additional components whose presence is advantageous, for example, leader sequences and fusion partner sequences. Expression control sequences can include a promoter.

Fibroblast Growth Factor (FGF): A large family of multigene family of growth factors that is a pleiotropic regulator of the proliferation, differentiation, migration, and survival in a variety of cell types (see Bikfalvi et al., Endocrine Rev. 18:26-45, 1997). The proteins in this family are 16-18 kDa proteins controlling normal growth and differentiation of mesenchymal, epithelial, and neuroectodermal cell types.

Two main groups of FGF are known. One type of FGF was isolated initially from brain tissue and identified by its ability to enhance proliferation of murine fibroblasts. Due to its basic pI the factor was named basic FGF or FGF-2 (see below) This factor is the prototype of the FGF family. Another factor, isolated also initially from brain tissues, has the ability to enhance proliferation of myoblasts. This factor is termed acidic FGF (aFGF). Other proteins in the FGF family are int-2 (FGF-3), FGF-4 FGF-5, FGF-6, K-FGF (FGF-7) and FGF-8. All of these factors are products of different genes. Some FGF are not secreted (FGF-2) while others (FGF-3, FGF-4, FGF-5 and FGF-6) have a signal sequence and therefore are secreted. Presently there are 23 factors identified as an FGF (numbered FGF-1 to FGF-23).

Basic fibroblast growth factor ("b-FGF" or "FGF-2") is a potent stimulator of angiogenesis (see D'Amore and Smith, Growth Factors 8:61-75, 1993) and hematopoiesis in vivo (see Allouche and Bikfalvi, Prog. Growth Factor Res. 6:35-48, 1995). FGF-2 is also involved in organogenesis (Martin, Genes Dev. 12:1571-1586, 1998), vascularization (see Friesel and Maciag, FASEB J. 9:919-925, 1995), and wound healing (see Ortega et al., Proc. Natl. Acad. Sci. USA 95:5672-5677, 1998), and plays an important role in the differentiation and/or function of various organs, including the nervous system (see Ortega et al., Proc. Natl. Acad. Sci. USA 95:5672-5677, 1998), and the skeleton (see Montero et al., J. Clin. Invest. 105:1085-1093, 2000). Because of its angiogenic and anabolic properties, FGF-2 has been shown to be involved in wound healing.

Fracture: A medical condition in which a bone is cracked or broken; a break in the continuity of a bone. Fractures may be classified as closed or open. A closed fracture is one in which the skin is intact; an open (or compound) fracture is one in which the bone is in contact with the air (such as piercing the skin or due to severe tissue injury). Fractures are also classified as simple or multi-fragmentary. A simple fracture occurs along only one line (such as splitting a bone into two pieces), while a multi-fragmentary fracture splits a bone into multiple pieces (such as three or more pieces). Other types of fracture include complete, incomplete, linear, transverse, oblique, compression, spiral, comminuted, and compacted fractures. Additional fractures include a critical defect (such as when part of a bone is lost or removed) and a non-union fracture (such as when the ends of the fracture are not in contact with each other).

Gel: A state of matter between liquid and solid, and is generally defined as a cross-linked polymer network swollen in a liquid medium. Typically, a gel is a two-phase colloidal dispersion containing both solid and liquid, wherein the amount of solid is greater than that in the two-phase colloidal dispersion referred to as a "sol." As such, a "gel" has some of the properties of a liquid (i.e., the shape is resilient and deformable) and some of the properties of a solid (for example, the shape is discrete enough to maintain three dimensions on a two dimensional surface). "Gelation time," also referred to as "gel time," refers to the time it takes for a composition to become non-flowable under modest stress.

Heterologous: A heterologous sequence is a sequence that is not normally (i.e. in the wild-type sequence) found adjacent to a second sequence. In one embodiment, the sequence is from a different genetic source, such as a virus or organism, than the second sequence.

Host cells: Cells in which a vector can be propagated and its DNA expressed. The cell may be prokaryotic or eukaryotic. The term also includes any progeny of the subject host cell. It is understood that all progeny may not be identical to the parental cell since there may be mutations that occur during replication. However, such progeny are included when the term "host cell" is used.

Hyaluronan (Hyaluronic Acid): An anionic, nonsulfated glycosaminoglycan distributed widely in vivo throughout connective, epithelial, and neural tissues. It is unique among glycosaminoglycans in that it is nonsulfated, and forms in the plasma membrane instead of the Golgi apparatus. Hyaluronic acid is a polymer of disaccharides, themselves composed of D-glucuronic acid and D-N-acetylglucosamine, linked via alternating β-1,4 and β-1,3 glycosidic bonds. Hyaluronic acid can be 25,000 disaccharide repeats in length. Polymers of hyaluronic acid can range in size from 5,000 to 20,000,000 Da in vivo.

Hydrogel: A solid, jelly-like material having a controlled cross-linked structure exhibiting no flow when in the steady state. A hydrogel can be a water-swellable polymeric matrix that can absorb a substantial amount of water to form an elastic gel, wherein "matrices" are three-dimensional networks of macromolecules held together by covalent or noncovalent crosslinks. Upon placement in an aqueous environment, dry hydrogels swell to the extent allowed by the degree of cross-inking.

Immune response: A response of a cell of the immune system, such as a B cell, T cell, neutrophil, macrophage or monocyte, to a stimulus. In one embodiment, the response is specific for a particular antigen (an "antigen-specific response"). In one embodiment, an immune response is a T cell response, such as a CD4+ response or a CD8+ response. In another embodiment, the response is a B cell response, and results in the production of specific antibodies.

Inhibiting or treating a disease: Inhibiting the full development of a disease or condition or accelerating healing, for example, in a subject who is at risk for a disease (for example, atherosclerosis or cancer). "Treatment" refers to a therapeutic intervention that ameliorates a sign or symptom of a disease or pathological condition after it has begun to develop. Treatment can also refer to acceleration of fracture healing. As used herein, the term "ameliorating," with reference to a disease or pathological condition, refers to any observable beneficial effect of the treatment. The beneficial effect can be evidenced, for example, by a delayed onset of clinical symptoms of the disease in a susceptible subject, a reduction in severity of some or all clinical symptoms of the disease, such as pain, a shortened recovery time or an improvement in the overall health or well-being of the subject, or by other parameters well known in the art that are specific to the particular disease.

Isolated: An "isolated" biological component (such as a nucleic acid or protein or cell) has been substantially separated or purified away from other biological components in the cell of the organism, or other cells, in which the component naturally occurs. Nucleic acids and proteins that have been "isolated" include nucleic acids and proteins purified by standard purification methods. The term also embraces nucleic acids and proteins prepared by recombinant expression in a host cell as well as chemically synthesized nucleic acids.

Label: A detectable compound or composition that is conjugated directly or indirectly to another molecule, such as an antibody or a protein, to facilitate detection of that molecule. Specific, non-limiting examples of labels include fluorescent tags, enzymatic linkages, and radioactive isotopes.

Mammal: This term includes both human and non-human mammals. Similarly, the term "subject" includes both human and veterinary subjects.

Mesenchymal Stem Cell (MSC): A multipotent stem cell capable of giving rise to differentiated cells in multiple mesenchymal lineages, specifically to osteoblasts, adipocytes, myoblasts, and chondrocytes. Generally, MSCs also have one or more of the following properties: an ability to undergo asynchronous, or asymmetric replication (where the two daughter cells after division can have different phenotypes); extensive self-renewal capacity; and clonal regeneration of the tissue in which they exist, for example, the non-hematopoietic cells of bone marrow. A cell can be classified as an MSC if it shows plastic adherent properties under normal culture conditions and has a fibroblast-like morphology, and can undergo osteogenic, adipogenic and chondrogenic differentiation ex-vivo.

MSCs can be cryopreserved. MSCs have been shown to engraft and selectively differentiate, based on the tissue environment. Due to their cellular origin and phenotype, these cells do not provoke an adverse immune response, allowing for the development of products derived from unrelated donors.

Methacrylate: Methacrylic acid and derivatives thereof. These derivatives include the parent acid ($CH_2C(CH_3)CO_2H$), salts (e.g., $CH_2C(CH_3)CO_2^-Na^+$), esters (e.g. $CH_2C(CH_3)CO_2CH_3$, or methyl methacrylate) and the polymers of these species.

Nucleic acid: A polymer composed of nucleotide units (ribonucleotides, deoxyribonucleotides, related naturally occurring structural variants, and synthetic non-naturally occurring analogs thereof) linked via phosphodiester bonds, related naturally occurring structural variants, and synthetic non-naturally occurring analogs thereof. Thus, the term includes nucleotide polymers in which the nucleotides and the linkages between them include non-naturally occurring synthetic analogs, such as, for example and without limitation, phosphorothioates, phosphoramidates, methyl phosphonates, chiral-methyl phosphonates, 2-O-methyl ribonucleotides, peptide-nucleic acids (PNAs), and the like. Such polynucleotides can be synthesized, for example, using an automated DNA synthesizer. The term "oligonucleotide" typically refers to short polynucleotides, generally no greater than about 50 nucleotides. It will be understood that when a nucleotide sequence is represented by a DNA sequence (i.e., A, T, G, C), this also includes an RNA sequence (i.e., A, U, G, C) in which "U" replaces "T."

Conventional notation is used herein to describe nucleotide sequences: the left-hand end of a single-stranded nucleotide sequence is the 5'-end; the left-hand direction of a double-stranded nucleotide sequence is referred to as the 5'-direction. The direction of 5' to 3' addition of nucleotides to nascent RNA transcripts is referred to as the transcription direction. The DNA strand having the same sequence as an mRNA is referred to as the "coding strand." Sequences on a nucleic acid sequence which are located 5' to sequence of interest are referred to as "upstream sequences;" sequences a nucleotide sequence which are located 3' to the sequence of interest are referred to as "downstream sequences."

"Encoding" refers to the inherent property of specific sequences of nucleotides in a polynucleotide, such as a gene, a cDNA, or an mRNA, to serve as templates for synthesis of other polymers and macromolecules in biological processes having either a defined sequence of nucleotides (for example, rRNA, tRNA and mRNA) or a defined sequence of amino acids and the biological properties resulting therefrom. Thus, a gene encodes a protein if transcription and translation of mRNA produced by that gene produces the protein in a cell or other biological system. Both the coding strand, the nucleotide sequence of which is identical to the mRNA sequence and is usually provided in sequence listings, and non-coding strand, used as the template for transcription, of a gene or cDNA can be referred to as encoding the protein or other product of that gene or cDNA. Unless otherwise specified, a "nucleotide sequence encoding an amino acid sequence" includes all nucleotide sequences that are degenerate versions of each other and that encode the same amino acid sequence. Nucleotide sequences that encode proteins and RNA may include introns.

"Recombinant nucleic acid" refers to a nucleic acid having nucleotide sequences that are not naturally joined together, such as in a wild-type gene. This includes nucleic acid vectors comprising an amplified or assembled nucleic acid which can be used to transform a suitable host cell. In one example, a recombinant nucleic acid is one that has a sequence that is not naturally occurring or has a sequence that is made by an artificial combination of two otherwise separated segments of sequence. This artificial combination is often accomplished by chemical synthesis or, more commonly, by the artificial manipulation of isolated segments of nucleic acids, such as by genetic engineering techniques. A host cell that includes the recombinant nucleic acid is referred to as a "recombinant host cell." A recombinant nucleic acid may serve a non-coding function (such as a promoter, origin of replication, ribosome-binding site, etc.) as well.

A first sequence is an "antisense" with respect to a second sequence if a polynucleotide whose sequence is the first sequence specifically hybridizes with a polynucleotide whose sequence is the second sequence. Thus, the two sequences are complementary.

Osteoblast: A mononucleate cell that is responsible for bone formation. Osteoblasts produce an osteoid matrix, which is composed mainly of collagen type I. Osteoblasts are also responsible for mineralization of the osteoid matrix. Bone is a dynamic tissue that is constantly being reshaped by osteoblasts, which build bone, and osteoclasts, which resorb bone. Osteoblasts arise from osteoprogenitor cells located, for example, in the periosteum and the bone marrow. Osteoprogenitors are immature progenitor cells that express the master regulatory transcription factor Cbfa1/Runx2. Once osteoprogenitors start to differentiate into osteoblasts, they begin to express a range of markers including osterix, collagen type 1, alkaline phosphatase, osteocalcin, osteopontin, and osteonectin.

Osteoclast: A type of bone cell that removes bone tissue by removing its mineralized matrix by a process of bone resorption. Osteoclasts are formed by the fusion of cells of the monocyte-macrophage cell line. Osteoclasts are characterized by high expression of tartrate resistant acid phosphatase and cathepsin K.

Osteocyte: Mature, non-dividing bone cells that are housed in their own lacunae (small cavities in the bone). Osteocytes are derived from osteoblasts and they represent the final stage of maturation of the bone cell lineage. While osteocytes are metabolically less active than osteoblasts, they serve as the principal mechanosensing cells in bone, and are responsible for regulating the activity of bone-building osteoblasts and bone-resorbing osteoclasts in response to mechanical loading. The narrow, cytoplasmic processes of osteocytes remain attached to each other and to osteoblasts through canaliculi (small channels in the bone).

Osteoconduction: The scaffold function provided by the transplanted matrix biomaterial which facilitates cell attachment and migration, and therefore the distribution of a bone healing response throughout the grafted volume. This property is likely dependent on extracellular matrix molecules, such as those found in bone matrix, including collagens, fibronectin, vitronectin, osteonectin, osteopontin, osteocalcin, proteoglycans and others. Growth factors in the matrix may also play a role.

Osteomyelitis: Osteomyelitis is an infection in a bone. Infections can reach a bone by traveling through the bloodstream or spreading from nearby tissue. Osteomyelitis can also begin in the bone itself if an injury exposes the bone to bacteria.

Operably linked: A first nucleic acid sequence is operably linked with a second nucleic acid sequence when the first nucleic acid sequence is placed in a functional relationship with the second nucleic acid sequence. For instance, a promoter is operably linked to a coding sequence if the promoter affects the transcription or expression of the coding sequence. Generally, operably linked DNA sequences are contiguous and, where necessary to join two protein-coding regions, in the same reading frame.

Pharmaceutically acceptable carriers: The pharmaceutically acceptable carriers of use are conventional. Remington's Pharmaceutical Sciences, by E. W. Martin, Mack Publishing Co., Easton, Pa., 15th Edition, 1975, describes compositions and formulations suitable for pharmaceutical delivery of the fusion proteins herein disclosed.

In general, the nature of the carrier will depend on the particular mode of administration being employed. For instance, parenteral formulations usually comprise injectable fluids that include pharmaceutically and physiologically acceptable fluids such as water, physiological saline, balanced salt solutions, aqueous dextrose, glycerol or the like as a vehicle. For solid compositions (e.g., powder, pill, tablet, or capsule forms), conventional non-toxic solid carriers can include, for example, pharmaceutical grades of mannitol, lactose, starch, or magnesium stearate. In addition to biologically neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate.

Polymer: Molecules composed of repeating monomer units, including homopolymers, block copolymers, random copolymers, and graft copolymers. "Polymers" also include linear polymers as well as branched polymers, with branched polymers including highly branched, dendritic, and star polymers. A "polymerizing initiator" refers to any substance or stimulus, that can initiate polymerization of monomers or macromers by free radical generation. Exemplary polymerizing initiators include electromagnetic radiation, heat, and chemical compounds.

Polynucleotide: The term polynucleotide or nucleic acid sequence refers to a polymeric form of nucleotide at least 10 bases in length. A recombinant polynucleotide includes a polynucleotide that is not immediately contiguous with both of the coding sequences with which it is immediately contiguous (one on the 5' end and one on the 3' end) in the naturally occurring genome of the organism from which it is derived. The term therefore includes, for example, a recombinant DNA which is incorporated into a vector; into an autonomously replicating plasmid or virus; or into the genomic DNA of a prokaryote or eukaryote, or which exists as a separate molecule (for example, a cDNA) independent of other sequences. The nucleotides can be ribonucleotides, deoxyribonucleotides, or modified forms of either nucleotide. The term includes single- and double-stranded forms of DNA.

Polypeptide: Any chain of amino acids, regardless of length or post-translational modification (such as glycosylation or phosphorylation). A "residue" refers to an amino acid or amino acid mimetic incorporated in a polypeptide by an amide bond or amide bond mimetic, the "position" of the residue indicates its place in the amino acid sequence. A polypeptide has an amino terminal (N-terminal) end and a carboxy terminal end.

Promoter: A promoter is an array of nucleic acid control sequences that directs transcription of a nucleic acid. A promoter includes necessary nucleic acid sequences near the start site of transcription, such as, in the case of a polymerase II type promoter, a TATA element. A promoter also optionally includes distal enhancer or repressor elements which can be located as much as several thousand base pairs from the start site of transcription. Both constitutive and inducible promoters are included (see e.g., Bitter et al., *Methods in Enzymology* 153:516-544, 1987).

Specific, non-limiting examples of promoters include promoters derived from the genome of mammalian cells (for example, a metallothionein promoter) or from mammalian viruses (for example, the retrovirus long terminal repeat; the adenovirus late promoter, the vaccinia virus 7.5K promoter). Promoters produced by recombinant DNA or synthetic techniques may also be used. A polynucleotide can be inserted into an expression vector that contains a promoter sequence which facilitates the efficient transcription of the inserted genetic sequence of the host. The expression vector typically contains an origin of replication, a promoter, as well as specific nucleic acid sequences that allow phenotypic selection of the transformed cells.

Saccharide: A mono-, di-, tri-, or higher order saccharide or oligosaccharide. Representative monosaccharides include glucose, mannose, galactose, glucosamine, mannosamine, galactosamine, fructose, glyceraldehyde, erythrose, threose, ribose, arabinose, xylose, lyxose, allose, altrose, glucose, idose, talose, psicose, sorbose, and tagatose. Exemplary disaccharides include maltose, lactose, sucrose, cellobiose, trehalose, isomaltose, gentiobiose, melibiose, laminaribiose, chitobiose, xylobiose, mannobiose, sophorose, and the like. Certain tri- and higher oligosaccharides include raffinose, maltotriose, isomaltotriose, maltotetraose, maltopentaose, mannotriose, manninotriose, etc. Exemplary polysaccharides include starch, sodium starch glycolate, alginic acid, cellulose, carboxymethylcellulose, hydroxyethylcellulose, hydropropylcellulose, hydroxypropylmethylcellulose, ethylcellulose, carageenan, chitosan, chondroitin sulfate, heparin, hyaluronic acid, and pectinic acid. A "saccharide unit" refers to a saccharide molecule having at least one pyranose or furanose ring. In some embodiments, at least one hydrogen atom may be removed from a hydroxyl group of a saccharide unit, as when the hydroxyl group has been esterified.

Scaffold: A structure, usually comprising a biocompatible material, which provides a surface suitable for adherence and proliferation of cells, and also provides stability and support. A scaffold can be in a particular shape or form so as to influence or delimit a three-dimensional shape or form assumed by a population of proliferating cells. Such shapes or forms include, but are not limited to, films (e.g. a form with two-dimensions substantially greater than the third dimension), ribbons, cords, sheets, flat discs, cylinders, spheres, and amorphous shapes.

Therapeutically effective amount: A quantity of a specific substance, such as a stem cell, for example MSCs, sufficient to achieve a desired effect in a subject being treated. For instance, this can be the amount necessary to accelerate fracture healing. When administered to a subject, a dosage will generally be used that will achieve target tissue concentrations (for example, in bone) that has been shown to achieve a desired in vitro effect.

Transduced: A transduced cell is a cell into which has been introduced a nucleic acid molecule by molecular biology techniques. As used herein, the term transduction encompasses all techniques by which a nucleic acid molecule might be introduced into such a cell, including transfection with viral vectors, transformation with plasmid vectors, and introduction of naked DNA by electroporation, lipofection, and particle gun acceleration.

Transplanting: The placement of a biocompatible substrate, such as a hydrogel, into a subject in need thereof. The biocompatible substrate can include cells, such as MSCs.

Ultraviolet light: An electromagnetic radiation with a wavelength from 400 nm to 100 nm, shorter than that of visible light but longer than X-rays. This light includes ultraviolet A (UVA) from 320 to 400 nm, UVB from 290 to 320 nm, and UVC from 100 to 290 nm.

Vector: A nucleic acid molecule as introduced into a host cell, thereby producing a transformed host cell. A vector may include nucleic acid sequences that permit it to replicate in a host cell, such as an origin of replication. A vector may also include one or more selectable marker genes and other genetic elements known in the art. Vectors can be viral vectors, such as adenoviral, retroviral, or lentiviral vectors. Vectors can be non-viral vectors, such as Sleeping Beauty plasmids or Prince Charming plasmids.

Visible light: A form of electromagnetic (EM) radiation that can be seen by human eyes. Visible light falls in the range of the EM spectrum between infrared (IR) and ultraviolet (UV). It has frequencies of about $4\times10^{14}$ to $8\times10^{14}$ cycles per second, or hertz (Hz) and wavelengths of about 740 nanometers (nm) or $2.9\times10^{-5}$ inches, to 380 nm ($1.5\times10^{-5}$ inches).

Unless otherwise explained, all technical and scientific terms used herein have the same meaning as commonly understood by one of ordinary skill in the art to which this disclosure belongs. The singular terms "a," "an," and "the" include plural referents unless context clearly indicates otherwise. Similarly, the word "or" is intended to include "and" unless the context clearly indicates otherwise. It is further to be understood that all base sizes or amino acid sizes, and all molecular weight or molecular mass values, given for nucleic acids or polypeptides are approximate, and are provided for description. Although methods and materials similar or equivalent to those described herein can be used in the practice or testing of this disclosure, suitable methods and materials are described below. The term "comprises" means "includes." All publications, patent applications, patents, and other references mentioned herein are incorporated by reference in their entirety. In case of conflict, the present specification, including explanations of terms, will control. In addition, the materials, methods, and examples are illustrative only and not intended to be limiting.

Mesenchymal Stem Cells

Avian mesenchymal cells (MSC) are used in the methods disclosed herein. MSC can be isolated from bone marrow or another source, such as adipose tissue. These MSC can be identified by functional assays both in vitro and in vivo, particularly assays relating to the ability of stem cells to give rise to multiple differentiated progeny and their ability to form clonal colonies. The MSC which are employed may be fresh, frozen, or have been subject to prior culture. They may be embryonic, neonate, or adult.

Generally, avian MSC are of use in the methods disclosed herein. The MSC can be autologous, such as from the same bird, or allogeneic, such as a different bird of the same species, or xenogeneic, such as from a different bird of a different species.

Bone marrow cells may be obtained from iliac crest, femora, tibiae, spine, rib or other medullary spaces. Other sources of MSC may include embryonic yolk sac, periosteum, fetal and adolescent skin, peripheral blood, and placenta and umbilicus (in mammals).

As a non-limiting example, bone marrow derived MSC may be separated from hematopoietic cells by plating isolated cells on treated polystyrene tissue culture dishes. This allows MSC to attach, while the hematopoietic cells remain in suspension, floating in the dish. The isolation medium may be aspirated, such as about two to three days following plating, and replaced with fresh isolation media. The cells may be serially passaged two or more times to ensure complete removal of any contaminating cells such as hematopoietic cells. Prior to reaching confluence, cells may be subcultured by first washing cells with a sterile solution, e.g., physiological saline, followed by the addition of a solution comprising trypsin, which may be an animal free product. In some embodiments, MSC can be maintained culture for at least 10-20 passages. Other methods of isolating MSC, e.g., from adipose tissue or from any other tissue that contains MSC, are known in the art.

MSC may be isolated by fluorescence activated cell sorting (FACS). As a non-limiting example, bone marrow derived cells may be stained with an antibody specific for an MSC marker, and separated on the basis of expression of that marker. For example, for mammalian MSC, in one embodiment, MSC may be isolated from other cells by staining with Stro-1. Non-limiting examples of MSC markers that may be used to confirm isolation of MSC by FACS, or other similar methods, include Stro-1, CD146, CD271, CD56, CD200, CD349, Soxl 1, CD73, CD44, CD73, CD90, CD105, and others. Avian MSC have been reported to express CD44, CD71, and CD73 (Gao et al., Biomed Res Int. 2013; 2013:626258. doi: 10.1155/2013/626258. Epub 2013, incorporated herein by reference).

Analysis of MSC markers can be performed using well-known methods (e.g., flow cytometric analysis, Western blot analysis, RT-PCR, in situ hybridization, immunofluorescence, immunohistochemistry, etc). Analysis of MSC proliferation may be performed using well-known methods, e.g., BrdU incorporation.

Chicken MSC have been produced, see Gao et al., "Isolation and characterization of chicken dermis-derived mesenchymal stem/progenitor cells," Biomed Res Int. 2013; 2013:626258. doi: 10.1155/2013/626258. Epub 2013 Aug. 4; Kocamaz et al., "Implication of C-type natriuretic peptide-3 signaling in glycosaminoglycan synthesis and chondrocyte hypertrophy during TGF-β1 induced chondrogenic differentiation of chicken bone marrow-derived mesenchymal stem cells," J Mol Histol. 2012 October; 43(5):497-508. doi: 10.1007/s10735-012-9430-2. Epub 2012 Jun. 20; and Bai et al, "Biological characterization of chicken mesenchymal stem/progenitor cells from umbilical cord Wharton's jelly," Mol Cell Biochem. 2013 April; 376(1-2):95-102. doi: 10.1007/s11010-012-1553-y, Epub 2012 Dec. 30. Erratum in: Mol Cell Biochem. 2013 April; 376(1-2):199, all of which are incorporated by reference herein.

MSC can be propagated continuously in culture, using culture conditions that promote proliferation without promoting differentiation, using methods known in the art. The cells can be maintained in medium, such as, but not limited to, Dulbecco's Modified Eagle's Medium (DMEM); in the presence of fetal bovine serum or serum-free replacement without differentiation. Generally the cells may be passaged at about 75% confluence, using a protease, e.g. trypsin, collagenase, etc. In one embodiment, MSC are propagated continuously in MSC proliferation medium, e.g., DMEM, fetal calf serum (e.g., at a concentration of about 0-10%), and antibiotics such as penicillin/streptomycin (pen/strep; e.g., at a concentration of about 100 units/ml). In embodiments where fetal calf serum and/or horse serum are undesirable, fibroblast growth factor (bFGF, e.g., at about 0-100 ng/ml) can be used.

MSC can be differentiated in a growth environment that enriches for cells with the desired phenotype, such as osteoblasts, adipocytes, and chondrocytes. The culture can include agents that enhance differentiation to a specific lineage.

In some embodiments, the MSC are transfected so that they express an exogenous nucleic acid molecules, such as encoding a growth factor, for example, an FGF or a BMP. The nucleic acid can be operably linked to a heterologous promoter to provide expression in avian cells.

DNA or RNA viral vectors include an attenuated or defective DNA or RNA viruses. In some embodiments, the vector is an avian RCAS retrovirus (DeLise and Tuan, J Cell Biochem. 2002; 87(3):342-59).

Use of defective viral vectors allows for administration to cells in a specific, localized area, without concern that the vector can infect other cells. Thus, a specific tissue can be specifically targeted.

Genes can also be introduced in a retroviral vector (e.g., as described in U.S. Pat. Nos. 5,399,346, 4,650,764, 4,980,289 and 5,124,263; all of which are herein incorporated by reference; Mann et al., Cell 33:153, 1983; Markowitz et al., J. Virol., 62:1120, 1988; PCT Application No. PCT/US95/14575; European Patent Application No. EP 453242; European Patent Application No. EP178220; Bernstein et al. Genet. Eng., 7:235, 1985; McCormick, BioTechnol., 3:689, 1985; PCT Publication No. WO 95/07358; and Kuo et al. Blood 82:845, 1993). Most retroviruses are integrating viruses that infect dividing cells. The lentiviruses are integrating viruses that infect nondividing cells. The retrovirus genome includes two LTRs, an encapsidation sequence and three coding regions (gag, pol and env). In recombinant retroviral vectors, the gag, pol and env genes are generally deleted, in whole or in part, and replaced with a heterologous nucleic acid sequence of interest. The gag, pol and env genes are coexpressed in the packaging cell line.

Electroporation can be used to introduce nonviral vectors and other nucleic acids into cells and tissues in vivo (see DeLise and Tuan, Methods Mol Biol. 2000; 137:377-82; Song et al., Mol Ther. 2004 April; 9(4):607-16). Generally, in this method, a high concentration of vector DNA is added to a suspension of host cell and the mixture is subjected to an electrical field of approximately 200 to 600 V/cm. Following electroporation, transformed cells are identified by growth on appropriate medium containing a selective agent. Electroporation has also been effectively used in animals or humans (see Lohr et al., Cancer Res. 61:3281-3284, 2001; Nakano et al, Hum Gene Ther. 12:1289-1297, 2001; Kim et al., Gene Ther. 10:1216-1224, 2003; Dean et al. Gene Ther. 10:1608-1615, 2003; and Young et al., Gene Ther. 10:1465-1470, 2003).

In some embodiments, the MSC can be induced to differentiate in vitro, and the differentiated cells can be utilized. Osteogenic differentiation can be achieved by plating the MSC and culturing to confluency, then culturing in medium comprising β-glycerol phosphate, ascorbic acid and retinoic acid (see Caterson et al., Mol Biotechnol. 2002 March; 20(3):245-56; Cowan et al. (2005) Tissue engineering 11, 645-658). In other embodiments, adipogenic differentiation can be achieved by plating MSC and culturing to confluency, then culturing in medium comprising dexamethasone, indomethacin, 3-isobutyl-1-methylxanthine (IBMX), and insulin, then maintaining in growth media with insulin. In further embodiments, chondrocyte differentiation can be achieved by plating cells and culturing to confluency, then culturing in medium comprising dexamethasone, ascorbic acid 2-phosphate, insulin, transferrin, selenous acid, with or without TGF-.beta.1 (see Williams et al. (2003) Tissue Engineering 9(4):679). In yet other embodiments, myocyte differentiation can be achieved by plating cells and culturing to confluency, then culturing in medium comprising horse serum, dexamethasone, and hydrocortisone (see Eun et al. (2004) Stem Cells 22:617-624); or 5-azacytidine (see Fukuda et al. (2001) Artificial Organs 25:187).

Pharmaceutical compositions including the MSC are also of use in the method disclosed herein. The composition can also contain additional components, such as osteoinductive factors. Such osteoinductive factors include, for example, dexamethasone, ascorbic acid-2-phosphate, 3-glycerophosphate and/or transforming growth factor (TGF) superfamily proteins, such as the bone morphogenetic proteins (BMPs). The composition can also contain antibiotic, antimycotic, anti-inflammatory, immunosuppressive and other types of therapeutic, preservative and excipient agents.

Hydrogels

A pharmaceutical composition is also provided that includes a hydrogel. The hydrogel can be a gelatin, cellulose and/or collagen-based matrix in combination with bone marrow and/or isolated mesenchymal stem cells. Thus, the hydrogel can form a biocompatible scaffold for transplantation of mesenchymal stem cells. The composition is, for example, inserted in the defect, such as, but not limited to, a fracture, and results in osteogenic healing of the defect. The hydrogel can be a photocrosslinked gelatin hydrogel.

Hydrogels can generally absorb fluid and, at equilibrium, typically are composed of 60-90% fluid and only 10-30% polymer. In one embodiment, the water content of hydrogel is about 70-80%. Generally, a hydrogel is biocompatible. A hydrogel can be prepared by crosslinking hydrophilic biopolymers or synthetic polymers (see PCT Application No. WO 2013/040559, incorporated herein by reference). Examples of the hydrogels formed from physical or chemical crosslinking of hydrophilic biopolymers include, but are not limited to, hyaluronans, chitosans, alginates, collagen, dextran, pectin, carrageenan, polylysine, gelatin and/or agarose. (see.: W. E. Hennink and C. F. van Nostrum. 2002, Adv. Drug Del. Rev. 54, 13-36 and A. S. Hoffman. 2002, Adv. Drug Del. Rev. 43, 3-12). These materials consist of high-molecular weight backbone chains made of linear or branched polysaccharides or polypeptides. The hydrogel can include natural polymers or synthetic (non-natural) polymers.

In one embodiment, hydrogel is a non-biodegradable hydrogel, a natural biodegradable hydrogel, and/or a synthetic biodegradable hydrogel. In certain embodiments, the hydrogel is a self-assembly peptide, a fibrin, an alginate, an agarose, a hyaluronan, a hyaluronic acid, a chitosan, a chondroitin sulfate, a polyethylene oxide (PEO), a poly(ethylene glycol) (PEG), a collagen type I, a collagen type II hydrogel, or combination thereof. In a further embodiment, the hydrogel composition includes a hydrogel selected from the following: self-assembly peptide, fibrin, alginate, agarose, hyaluronan, hyaluronic acid, chitosan, chondroitin sulfate, collagen type I, collagen type II, and combinations thereof. In additional embodiments, the hydrogel includes bioabsorbable materials selected from gelatin, alginic acid, chitin, chitosan, dextran, polyamino acids, polylysine, and copolymers of these materials. In other embodiments, the hydrogel is manufactured from biodegradable materials which degrade in vivo or in vitro, at a sufficiently slow rate to allow the MSC to be therapeutically effective. The hydrogel can be made from alpha hydroxyl polyesters. Exemplary hydrogels are disclosed in U.S. Published Patent Application No. 2007/0098675 and U.S. Published Patent Application No. 2010/0179659, which are both incorporated herein by reference.

Examples of hydrogels based on chemical or physical crosslinking of synthetic polymers include but are not limited to (meth)acrylate-oligolactide-PEO-oligolactide-(meth)acrylate, poly(ethylene glycol) (PEO), poly(propylene glycol) (PPO), PEO-PPO-PEO copolymers (Pluronics), poly(phosphazene), poly(methacrylates), poly(N-vinylpyrrolidone), PL(G)A-PEO-PL(G)A copolymers, polyethylene imine), etc. (see A. S Hoffman, Adv. Drug Del. Rev, 43, 3-12, 2002). Hydrogels can be made degradable in vivo by incorporating PLA, PLGA or PGA polymers. Moreover, hydrogels can be modified with fibronectin, laminin, or vitronectin.

In one embodiment, the hydrogel scaffold includes gelatin. Hydrogels comprised of gelatin have a porous structure, helpful for the support of avian MSCs. Gelatin hydrogels are disclosed, for example, in Lin et al., Tissue Engineering Part A, DOI: 10.1089/ten.tea.2013.0642, 2014, incorporated herein by reference.

In additional embodiments, the hydrogel scaffold includes hyaluronan. The hydrogel scaffold can include gelatin and hyaluronan. In some embodiments, the hydrogel scaffold is prepared by methacrylation of the polymer and then utilizing a photoactivated initiator to start the crosslinking process. Method for producing these gelatin and hyaluronan scaffolds are known in the art and as discussed briefly below.

Altering molecular weights, block structures, degradable linkages, and cross-linking modes can influence strength, elasticity, and degradation properties of the hydrogels (Nguyen and West, 2002, Biomaterials 23(22):4307-14; Ifkovits and Burkick. 2007, Tissue Eng. 13(10):2369-85). Hydrogels can also be modified with functional groups for covalently attaching a variety of proteins (e.g., collagen) or compounds such as therapeutic agents. Therapeutics agents which can be linked to the matrix include, but are not limited to, analgesics, anesthetics, antifungals, antibiotics, anti-inflammatories, antidotes, antihistamines, antimicrobials, antiseptics, anti-arthritics, antivirals, chemotherapeutic agents, a colored or fluorescent imaging agent, corticoids (such as steroids), diagnostic aids, diuretics, enzymes, hormones, minerals, nutritional supplements, a radioisotope, sedatives, sulfonamides, stimulants, tranquilizers, vitamins, and growth factors. The therapeutic agent can also be other small organic molecules, naturally isolated entities or their analogs, organometallic agents, chelated metals or metal salts, peptide-based drugs, or peptidic or non-peptidic receptor targeting or binding agents.

A therapeutic agent can be linked to the hydrogel via a protease sensitive linker or other biodegradable linkage. Molecules which can be incorporated into the hydrogel include, but are not limited to, glycoproteins, fibronectin; peptides and proteins; carbohydrates (both simple and/or complex); proteoglycans; antigens; oligonucleotides (sense and/or antisense DNA and/or RNA); antibodies (for example, to infectious agents, tumors, drugs or hormones); and growth. In one embodiment, the hydrogel includes molecules that aid in the growth and proliferation of a mesenchymal stem cell, when cultured in or on the hydrogel. Non-limiting examples of such molecules can include proteins, peptides, supplements, small molecule inhibitors, glycosaminoglycans, growth factors, nucleic acid sequences, and combinations thereof. These molecules can be a growth factor.

In one non-limiting example, the growth factor is transforming growth factor $\beta$. Members of the transforming growth factor (TGF) supergene family, which are multifunctional regulatory proteins, can be utilized. Members of the TGF supergene family include TGF-$\beta$, (for example, TGP-$\beta$1, TGF-$\beta$2, TGF-$\beta$3); bone morphogenetic proteins (for example, BMP-1, BMP-2, BMP-3, BMP-4, BMP-5, BMP-6, BMP-7, BMP-8, BMP-9); heparin-binding growth factors (for example, fibroblast growth factor (FGF), epidermal growth factor (EGF), platelet-derived growth factor (PDGF), insulin-like growth factor (IGF)), Inhibins (for example, Inhibin A, Inhibin B), growth differentiating factors (for example, GDF-1); and Activins (for example, Activin A, Acivin B, Activin AB). In another non-limiting example, the growth factor is a bone morphogenic protein. Growth factors can be isolated from native or natural sources, such as from mammalian cells, or can be prepared synthetically, such as by recombinant DNA techniques or by various chemical processes. In addition, analogs, fragments, or derivatives of these factors can be used, provided that they exhibit at least some of the biological activity of the native molecule. For example, analogs can be prepared by expression of genes altered by site-specific mutagenesis or other genetic engineering techniques.

In certain embodiments, one or more multifunctional cross-linking agents may be utilized as reactive moieties that covalently link biopolymers or synthetic polymers. Such bifunctional cross-linking agents may include glutaraldehyde, epoxides (e.g., his-oxiranes), oxidized dextran, p-azidobenzoyl hydrazide, N-[a.-maleimidoacetoxy]succinimide ester, p-azidophenyl glyoxal monohydrate, bis-[-(4-azidosalicylamido)ethyl]disulfide, bis[sulfosuccinimidyl]suberate, dithiobis[succinimidyl proprionate, disuccinimidyl suberate, 1-ethyl-3-[3-dimethylaminopropyl]carbodiimide hydrochloride (EDC), N-hydroxysuccinimide (NHS) and other bifunctional cross-linking reagents known to those skilled in the art.

Methacrylic anhydride, methacryloyl chloride, and glycidyl methacrylate may be used to add methacrylate groups to one or more monomers of a polymer. Glycidyl methacrylate may be used, for example, for efficiency of reaction.

Polymerizing initiators include electromechanical radiation. Initiation of polymerization may be accomplished by irradiation with visible light, such as 380 to 740 nm, such as about 350 to about 700 nm, such as between about 514 nm and about 365 nm, such as about 380 nm. In some embodiments, the light intensity is about 10 m W/cm$^3$. In some embodiments, polymerization can also include cross-linking with ultraviolet light, such as UVA, UVB, and/or UVC light.

The mechanical properties of a cross-linked polymer matrix, such as a hydrogel may also be related to pore structure. For applications in tissue engineering, scaffolds with different mechanical properties may be desirable depending on the desired clinical application. For example, scaffolds for cartilage tissue engineering in the articular joint must survive higher mechanical stresses than a cartilage tissue engineering system implanted subcutaneously for plastic surgery applications. Thus, hydrogels with mechanical properties that are easily manipulated may be produced.

In one embodiment utilizing a cross-linking agent, polyacrylated materials, such as ethoxylated (20) trimethylpropane triacrylate, can be used as a photo-activated cross-linking agent. Components of an exemplary reaction mixture would include a thermoreversible hydrogel held at 39° C., polyacrylate monomers, such as ethoxylated (20) trimethylpropane triacrylate, a photo-initiator, such as eosin Y, catalytic agents, such as 1-vinyl-2-pyrrolidinone, and triethanolamine. Exposure of this reactive mixture to long-wavelength light (>498 nm) produces a cross-linked hydrogel.

In some embodiments, the hydrogel is a methacrylated gelatin hydrogel, such as a methacrylated hyaluronan (hyaluronic acid) hydrogel. The hydrogel can be a mixture of methacrylated gelatin and methacrylated hyaluronan. The hydrogel can be a gelatin hydrogel, such as a methacrylated gelatin, and/or methacrylated hyaluronan hydrogel that was photocrosslinked with visible light.

A photocrosslinked gelatin can be crosslinked using visible light. Suitable hydrogels are disclosed, for example, in Lin et al., Application of visible light-based projection stereolithography for live cell scaffold fabrication with designed architecture, Biomaterials. 2013 January; 34(2): 331-9. doi: 10.1016/j.biomaterials.2012.09.048. Epub 2012 Oct. 22, and Lin et al., Cartilage Tissue Engineering Application of Injectable Gelatin Hydrogel with In Situ Visible-Light-Activated Gelation Capability in both Air and Aqueous Solution, Tissue Eng Part A. 2014 Apr. 9, which are both incorporated herein by reference.

A cross-linked hydrogel matrix can be further stabilized and enhanced through the addition of one or more enhancing agents. Enhancing agents include any compound added to the hydrogel matrix, in addition to the high molecular weight components, that enhances the hydrogel matrix by providing further stability or functional advantages. These include, for example, polar amino acids, amino acid analogues, amino acid derivatives, intact collagen, and divalent cation chelators, such as ethylenediaminetetraacetic acid (EDTA) or salts thereof. Polar amino acids are intended to include tyrosine, cysteine, serine, threonine, asparagine, glutamine, aspartic acid, glutamic acid, arginine, lysine, and histidine. In specific non-limiting examples, one or more of L-cysteine, L-glutamic acid, L-lysine, and/or L-arginine is utilized. An enhancing agent can be added to the matrix composition before or during the crosslinking of the high molecular weight components.

MSCs can be expanded for inclusion in the hydrogel. A subculture of the MSCs can be made when cells become subconfluent or confluent. The subculture may be carried out as known in the art. For example, cells are detached from the surface of the culture container by treating with trypsin-EDTA and then collected. Culture solution is added to the collected cells to create a cell suspension. Centrifugation can be carried out when or after cells have been collected to provide a high cell density of cells. Common conditions for centrifugation include 500 rpm (30 g) to 1000 rpm (70 g) and 1 to 10 minutes. In some embodiments, a cloning ring or cloning cylinder is used to hold the cell suspension on the scaffold, keeping the cell suspension from flowing away from the scaffold during seeding. In some embodiments, $1\times10^6$ to $5\times10^7$ cells are utilized. In other embodiments, $2\times10^6$ to $2\times10^7$ cells are utilized. Culturing of the cell comprising scaffold may be done in any conditions that promote growth and proliferation of the cell population. Cells can be cultured in serum or in serum-free medium that includes specific growth factors.

Plasticizers and stabilizing agents known in the art may be incorporated in compositions. Buffers, acids and bases may be incorporated in the compositions to adjust their pH. Agents to increase the diffusion distance of agents released from the composition may also be included.

In one specific non-limiting example, MSCs ($4-20\times10^6$/ml) are seeded in a hydrogel, such as a gelatin/hydroxyapatite hydrogels produced by photocrosslinking, and cultured in BMP-2 included osteogenic media. Cartilage can be engineered by seeding MSCs ($4-60\times10^6$/ml) in gelatin/hyaluronic acid hydrogel by photocrosslinking, and treated with transforming growth factor-β 3 (TGF-β3) included chondrogenic medium. In a specific non-limiting example, osteochondral interfaces can be formed by placing layers of MSC-laden ($4-20\times10^6$/ml) gelatin hydrogels between the chondral and osseous-constructs.

Methods of Treatment

Methods are provided herein for treating a bone defect in a subject, wherein the subject is a bird. The method can promote cartilage repair and/or osteogenesis. In some embodiments, MSCs introduced into injured tissue sites exert a local anti-microbial effect. Thus, methods are provided for reducing fracture-related infection that can lead to bone infection, or osteomyelitis.

The methods include administering to the bone defect of the bird a therapeutically effective amount of avian MSC. The MSCs can be delivered alone or in combination with a matrix and/or other factors. Generally, the MSC are delivered locally, such as to the site of a bone defect.

The bird can have a fracture, such as a simple or compound fracture. Orthopedic classification of fractures includes closed or open and simple or multi-fragmentary fractures. In closed fractures the skin remains intact, whilst in an open fracture the bone may be exposed through the wound site, which brings a higher risk of infection. Simple fractures occur along a single line, tending to divide the bone in two. Multi-fragmentary fractures spilt the bone into multiple pieces. Other fracture types include, compression fracture, compacted fracture, spiral fracture, complete and incomplete fractures, transverse, linear and oblique fractures and comminuted fractures. The disclosed methods are of use to treat any of these types of fracture. The fracture can be a skull fracture, a sternum fracture, a rib fracture, or a fracture of an extremity, such as a leg or a wing bone.

The bird can have a bone disease, such as osteogenesis imperfecta or a metabolic bone disease. The bird can have a cancer. The methods can be used to repair segmental defects, spinal fusions or non-unions and other bone defects.

The bird can have a congenital, genetic, and metabolic skeletal pathology, such as a disease that affects the growth plate of long bones (e.g., dyschondroplasia and chondrodystrophy), or a pathology that affects the structure and function of the joint articular cartilage (e.g., chondrosis). The bird can be have osteoporosis and/or osteopenia.

The methods can reduce fracture-related infection that can lead to bone infection, such as osteomyelitis and/or bacterial chondronecrosis with osteomyelitis (BCO). Thus, in some example, the methods prevent or treat a bone infection, such as osteomyelitis or BCO. In some example, the methods prevent or treat an infection with *Staphylococcus aureus*, *Escherichia coli*, a coagulase-negative *Staphylococci* or an *Enterococcus* species. The bone may be predisposed to infection due to a recent trauma that results in a blood clot or hemostasis. The osteomyelitis can be acute or chronic.

In specific non-limiting examples, the methods can be used to prevent or treat osteomyelitis in growth plates of long bones, such as the proximal growth plate of the femur and tibiotarsus. In some embodiments, use of MSCs results in a decrease of infection. This can be evaluated based on the lack of one or more symptoms of osteomyelitis (e.g., including but not limited to, pain in the bone, bone tenderness, and swelling or warmth) or a negative diagnosis based on one or more diagnostic tests (e.g., including but not limited to, a bone scan, blood culture, or culture of the infectious lesion). In some embodiments, the MSC are delivered directly to the site of infection.

The bird can be any type of bird, including a bird of the order Anseriformes (swans, geese and ducks), Apodiformes (swifts and hummingbirds), Caprimulgiformes (goatsuckers), Charadriiformes (shorebirds, gulls and terns), Ciconiformes (bitterns, herons, ibis and storks), Columbiformes (pigeons and doves), Coraciiformes (kingfishers), Falconiformes (birds of prey such as falcons), Galliformes (turkey and chicken), Gaviidae (loons), Passeriformes (Passerines such as the blackbird, thrush, warbler blackbird and sparrow), Pelicaniformes (boobies, pelicans, cormorants and anhingas). Phoenicopteriformes (flamingos), Piciformes (woodpeckers and allies). Podicipediformes (grebes), Psittqciformes (parrots and parakeets), and Strigidae (owls). An exemplary list of birds that can be treated can be found on the web, see nps.gov/ever/naturescience/birdspecieslist.htm, and birds.audubon.org/species, birds-of-north-America.net/list-of-north-american-birds.htnml, and birdchannel.com/bird-species/all_landing.aspx, as of Oct. 17, 2014, which are incorporated herein by reference. In specific, non-limiting examples, the bird is a chicken, turkey, duck, pigeon, parakeet, lovebird, or a canary. The bird can be a fancy bird, such as fancy pigeon, bred for various traits relating to size, shape, color and/or behavior. Fancy pigeons are disclosed, for example, in the Australian Fancy Pigeons book of standards and the European List of Breeds of Fancy Pigeons, see the world-wide web, file entente-ee.com/deutsch/sparten/tauben/Dateien/2012/ELRT%2011-06-2012_pdf.

In some embodiments, the bird can be a bird of prey. The bird can be a member of any of the families of birds of prey, such as Accipitridae (a hawk, an eagle, a buzzard, a kite or an Old World vulture), Pandionidae (such as an osprey), Sagittariidae (such as a secretary bird), Falconidae (such as a falcon, a caracara and a forest falcon), or Cathartidae (such as a New World Vulture). The bird can be a nocturnal bird of prey, such as a member of the family Strigidae (such as a typical owl) or Tyonidae (such as a barn owl or a bay owl).

In a specific non-limiting example, the bird is a falcon. The falcon can be a kestrel, a hobby, a peregrine falcon or a heierofalcon. Exemplary falcons are Malagasy kestrel (*Falco newtoni*), Seychelles kestrel (*Falco araea*), Mauritius kestrel (*Falco punctatus*), Spotted kestrel (*Falco moluccensis*), Nankeen kestrel or Australian kestrel (*Falco cenchroides*), Common kestrel (*Falco tinnunculus*), Rock kestrel (*Falco rupicolus*), Greater kestrel (*Falco rupicoloides*), Fox kestrel (*Falco alopex*), Lesser kestrel (*Falco naumanni*), Grey kestrel (*Falco ardosiaceus*), Dickinson's kestrel (*Falco dickinsoni*), Banded kestrel (*Falco zoniventris*), Red-necked falcon (*Falco chicquera*), African red-necked falcon (*Falco (chicquera) ruficollis*), Red-footed falcon (*Falco vespertinus*), Amur falcon (*Falco amurensis*), Eleonora's falcon (*Falco eleonorae*), Sooty falcon (*Falco concolor*), American kestrel or "sparrow hawk" (*Falco sparverius*), Aplomado falcon (*Falcofemoralis*), Merlin or "pigeon hawk" (*Falco columbarius*), Eurasian merlin (*Falco (columbarius) aesalon*), Bat falcon (*Falco rufigularis*), Orange-breasted falcon (*Falco deiroleucus*), Eurasian hobby (*Falco subbuteo*), African hobby (*Falco cuvierii*), Oriental hobby (*Falco severus*), Australian hobby or little falcon (*Falco longipennis*), New Zealand falcon or kārearea (*Falco novaeseelandiae*), Brown falcon (*Falco berigora*), Grey falcon (*Falco hypoleucos*), Black falcon (*Falco subniger*), Lanner falcon (*Falco biarmicus*), Laggar falcon (*Falcojugger*), Saker falcon *Falco cherrug*, Altai falcon (*Falco cherrug altaicus*), Gyrfalcon (*Falco rusticolus*), Prairie falcon (*Falco mexicanus*), Peregrine falcon *Falco peregrinus*, Peale's falcon (*Falco peregrinus pealei*), Pallid falcon (*Falco peregrinus cassini* var. *kreyenborgi*), Barbary falcon (*Falco (peregrinus) pelegrinoides*) and a Taita falcon (*Falco fasciinucha*).

In additional embodiments, the bird is a hawk, such as an *Accipiter* or a *Buteo* hawk. The hawk can be a member of the Genus *Accipiter*, such as a Northern goshawk (*A. gentilis*), Eurasian sparrowhawk (*A. nisus*), Grey-bellied hawk (*A. poliogaster*), Crested goshawk (*A. trivirgatus*), Sulawesi goshawk (*A. griseiceps*), Red-chested goshawk (*A. toussenelii*), African goshawk (*A. tachiro*), Chinese sparrowhawk (*A. soloensis*), Frances's sparrowhawk (*A. francesii*), Anjouan sparrowhawk (*Accipiter* francesiae *pusillus*), Spot-tailed sparrowhawk (*A. trinotatus*), Grey goshawk (*A. novaehollandiae*), Brown goshawk (*A. fasciatus*), Christmas goshawk (*Accipiter fasciatus natalis*), Pied goshawk (*A. albogularis*), Fiji goshawk (*A. rufitorques*), White-bellied goshawk (*A. haplochrous*), Moluccan goshawk (*A. henicogrammus*), Grey-headed goshawk (*A. poliocephalus*), New Britain goshawk (*A. princeps*), Black sparrowhawk, (*A. melanoleucus*), Henst's goshawk (*A. henstii*), Meyer's goshawk (*A. meyerianus*), Chestnut-flanked sparrowhawk (*A. castanilius*), Nicobar sparrowhawk (*A. butleri*), Levant sparrowhawk (*A. brevipes*), Slaty-mantled sparrowhawk (*A. luteoschistaceus*), Imitator sparrowhawk (*A. imitator*), Red-thighed sparrowhawk (*A. erythropus*), Little sparrowhawk (*A. minullus*), Japanese sparrowhawk (*A. gularis*), Dwarf sparrowhawk (*A. nanus*), Rufous-necked sparrowhawk (*A. erythrauchen*), Collared sparrowhawk (*A. cirrocephalus*), New Britain sparrowhawk (*A. brachyurus*), Vinous-breasted sparrowhawk (*A. rhodogaster*), Madagascar sparrowhawk (*A. madagascariensis*), Ovambo sparrowhawk (*A. ovampensis*), Rufous-chested sparrowhawk (*A. rufiventris*), Shikra (*A. badius*), Tiny hawk (*A. superciliosus*), Semicollared hawk (*A. collaris*), Sharp-shinned hawk (*A. striatus*), White-breasted hawk (*A. s. chionogaster*), Plain-breasted hawk (*A. s. ventralis*), Rufous-thighed hawk (*A. s. erythronemius*), Cooper's hawk (*A. cooperii*), Gundlach's hawk (*A. gundlachi*), Bicolored hawk (*A. bicolor*), or a Besra (*A. virgatus*). The hawk can be a member of the genus *Melierax*, such as a Gabar goshawk (*M. gabar*), Dark chanting goshawk (*M.*

*metabates*), Eastern chanting goshawk (*M. poliopterus*) or a Pale chanting goshawk (*M. canorus*). The hawk can be a member of the genus *Urotriorchis*, such as a Long-tailed hawk (*U. macrourus*). The hawk can be a member of the genus *Erythrotriorchis*, such as a Red goshawk (*E. radiatus*) or a Chestnut-shouldered goshawk (*E. buergersi*). The hawk can be a member of the genus *Megatriorchis* such as a Doria's goshawk (*M. doriae*).

The bird can be an endangered species.

Generally, avian MSC are of use in the methods disclosed herein. The MSC can be autologous, such as from the same bird, or allogeneic, such as a different bird of the same species, or a different bird of a different species. However, the MSC also can be from xenogeneic sources. The MSC can be derived from bone marrow cells, such as those obtained from iliac crest, femora, tibiae, spine, rib or other medullary spaces. The MSC can be derived from another source, such as embryonic yolk sac, placenta, umbilical cord, periosteum, fetal and adolescent skin, and blood.

Avian MSC can be provided as either homogeneous, culture-expanded preparations derived from whole-marrow (or other pre-natal or post-natal source of autologous or allogeneic MSC), from MSC-enriched or heterogeneous cultures or from cell lines. In some embodiments, they are administered in combination with an osteoinductive or other medium. In some examples, an effective dose of at least about $10^3$, such as about $10^4$, MSCs per milliliter of the composition. Generally, a sufficient number of cell is provided that repairs the bone or other tissue defect beyond that in a volume of whole marrow equivalent to that of the defect.

Additional agents can be administered to the subject, such as osteoinductive factors. Such osteoinductive factors include, for example, dexamethasone, ascorbic acid-2-phosphate, β-glycerophosphate and/or transforming growth factor (TGF) superfamily proteins, such as the bone morphogenic proteins (BMPs). The composition can also contain antibiotic, antimycotic, anti-inflammatory, immunosuppressive and other types of therapeutic, preservative and excipient agents.

Other components can be administered with the cells. In some embodiments, the component is a matrix that provides osteoconductive or osteoinductive properties. The MSC can be administered with any adaptable biocompatible structural material that lends itself to fabrication according to the demands of the end use. In some embodiments, the material is a synthetic structural material such as a biocompatible polymer. Biodegradable polymers are also of use. Those materials can be selected such that they are dissolved or resorbed by the body without the need for surgical removal procedures. Biocompatible, biodegradable materials useful in the grafts disclosed herein include polyglycolic acid (PGA), collagen type 1, Poly-DL-lactide-caprolactone (PCL), laminin, gelatin, and the like. The cells can be administered in an intervertebral disc, see PCT Publication No. WO 2008039530, which is incorporated herein by reference.

In some embodiments, the MSC are administered with a hydrogel, such as, but not limited to, a gelatin hydrogel. In some embodiments, the hydrogel is a methacrylated gelatin hydrogel that is crosslinked with exposure to visible light (see Lin et al., "Cartilage Tissue Engineering Application of Injectable Gelatin Hydrogel with In Situ Visible-Light-Activated Gelation Capability in both Air and Aqueous Solution," Tissue Engineering: Part A, 2014, incorporated herein by reference). The implant can be provided using open surgical techniques, arthroscopic techniques or percutaneous injection.

In some embodiments, an absorbable implant is provided to the site of the bone defect, containing isolated MSC and optionally a hydrogel, such as a gelatin hydrogel, such as a cross-linked gelatin hydrogel. In some embodiments, MSC are uniformly distributed within the hydrogel. In further embodiments, the hydrogel supports condrogenic differentiation, osteogenic differentiation, or both. In additional embodiments, a composition comprising MSCs and a methacrylated gelatin hydrogel that is cross-linked with visible light is administered to the subject. In other embodiments, the composition comprising MSCs and a methacrylated gelatin hydrogel that is cross-linked following administration to the subject. In some embodiments, the methacrylated gelatin hydrogel is cross-linked with visible light prior to administering the composition to the avian subject. In other embodiments, the methacrylated gelatin hydrogel is cross-linked with visible light following administering the composition to the avian subject.

In a specific non-limiting example of cell delivery via encapsulation in photocrosslinked matrix hydrogel, MSCs are suspended (~$20 \times 10^6$ cells/ml) in an activated extracellular matrix component, such as methacrylated gelatin, methacrylated collagen type I, and/or methacrylated hyaluronic acid, in the presence of a visible light sensitive photoinitiator, such as lithium phenyl-2,4,6-trimethylbenzoylphosphinate (LAP; 0.15%). Photocrosslinking or photopolymerization of the hydrogel is achieved by exposure of the cell-laden solution to visible light (430-490 nm, power 1400 mW/cm$^2$) for approximately 8 min.

The MSCs can be administered with other agents. Suitable agents include, but are not limited to, antibiotics and growth factor. Suitable antibiotics include, but are not limited to, ampicillin, tetracycline, chloramphenicol, erythromycin, trimethoprim/sulfa combinations, enrofloxacin, amikacin, cephalosportins (such as cefotaxime) and penicillins (such as piperacillin).

EXAMPLES

Disclosed herein is the isolation and multi-lineage differentiation potency of chick bone marrow mesenchymal stem cells (MSCs), and their application for skeletal tissue repair, specifically cartilage and bone. The results clearly demonstrate the osteogenic and chondrogenic capabilities of chick MSCs and their ability, when placed in a 3-dimensional hydrogel scaffold, to repair bone and cartilage defects. The results also demonstrate that bone marrow derived MSCs have antibacterial effects.

Example 1

Isolation of Chick Bone Marrow Mesenchymal Stem Cells

Figure 1B:
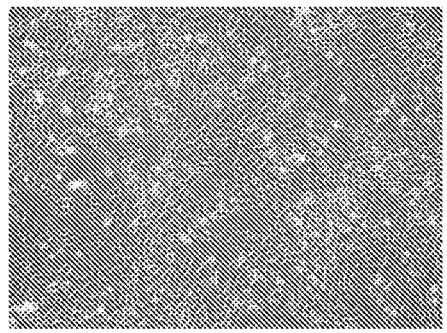
Figure 1C:
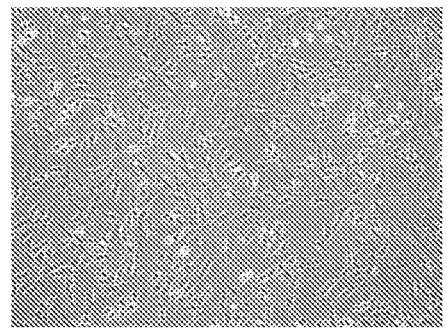
Figure 2A:
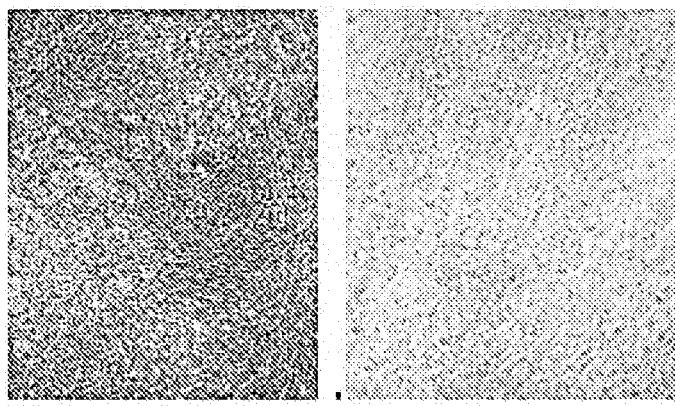
FIGS. 2A-2D. Chick MSCs undergoing induced osteogenic, chondrogenic, and adipogenic differentiation (day 8 of culture).
Figure 2B:
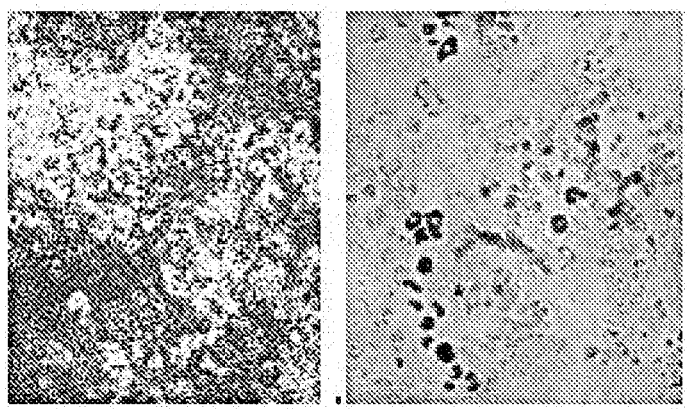
Figure 2C:
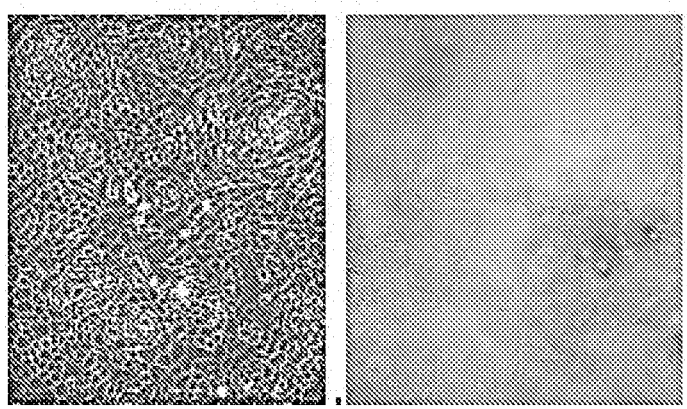
Figure 2D:
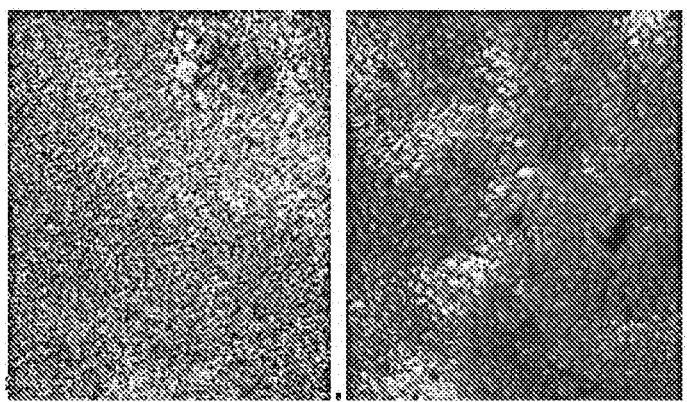
Figure 3:
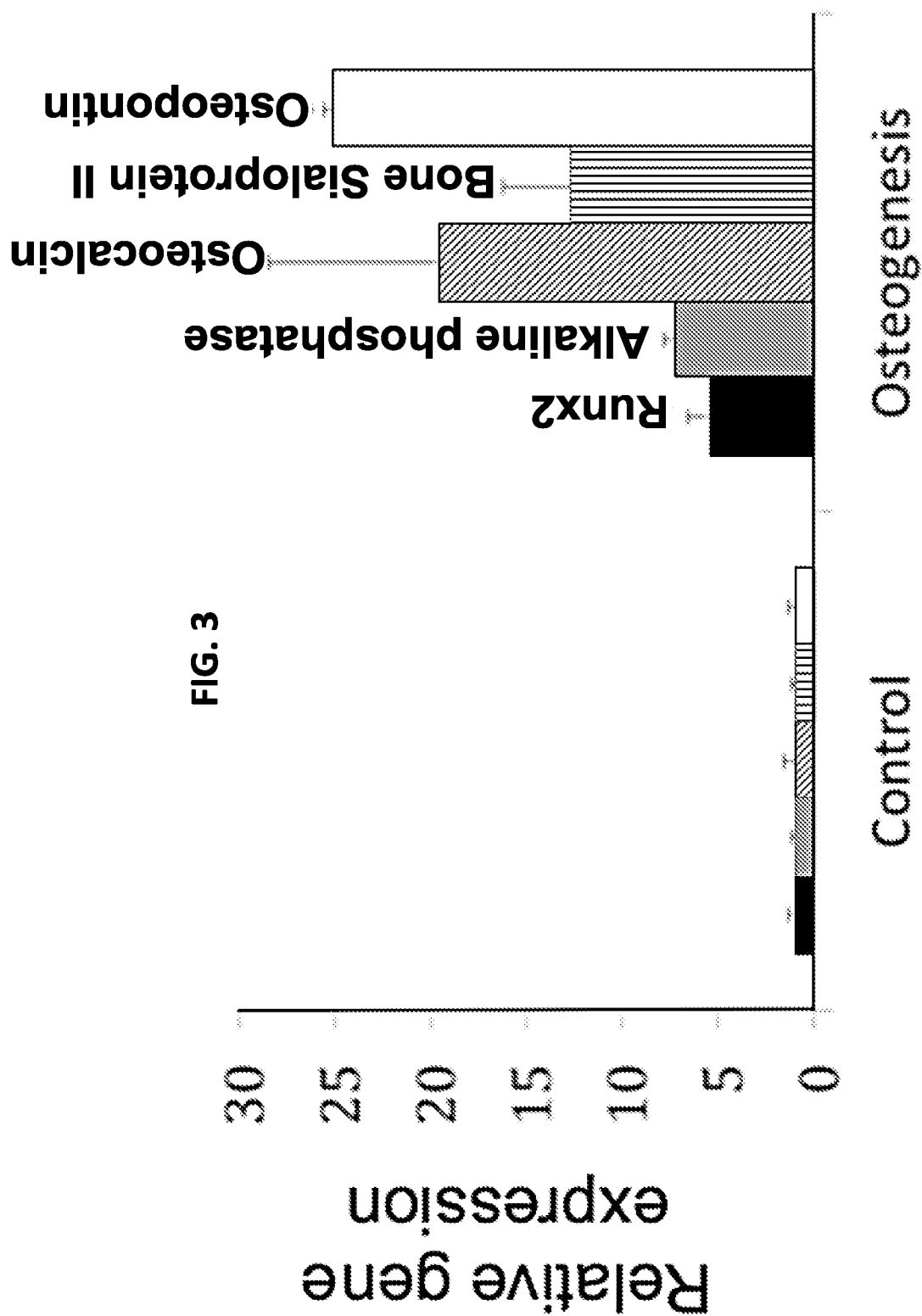
FIG. 3. Expression of osteogenesis-associated genes in chick MSCs undergoing induced osteogenic differentiation. Chick MSCs were placed into osteogenic culture and gene expression was analyzed at day 14 of culture by real-time reverse transcription polymerase chain reaction (RT-PCR). Glyceraldehyde-3-phosphate dehydrogenase (GAPDH) was used as the housekeeping gene standard. Chick MSCs underwent robust osteogenesis accompanied by highly elevated expression of the osteogenesis-associated genes, Runx2, alkaline phosphatase, osteocalcin, bone sialoprotine II, and collagen type I. Gene expression levels expressed relative to those in control, uninduced cultures.
Figure 4:
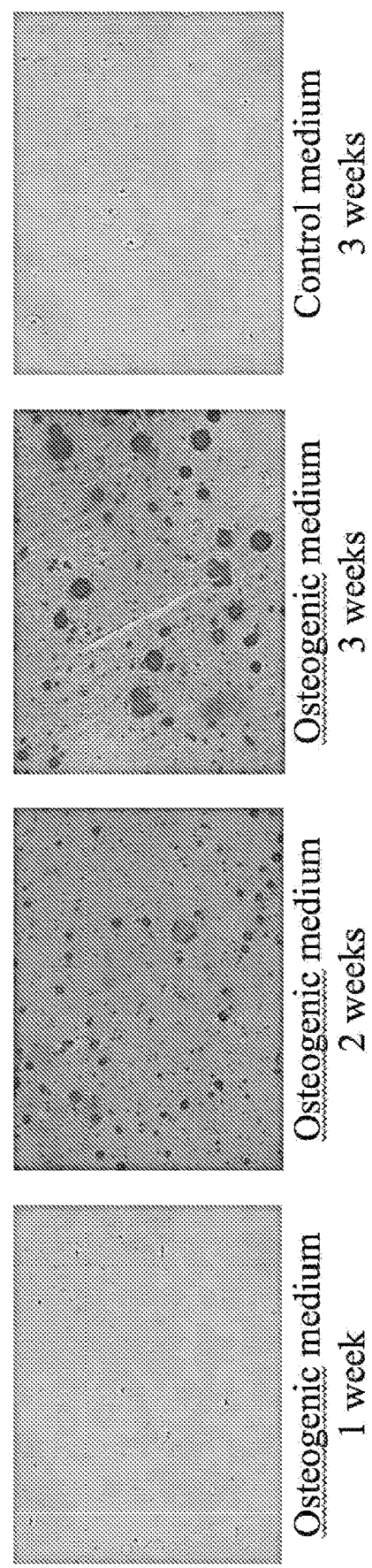
FIG. 4. Osteogenic activity of chicken MSCs in 3-dimensional hydrogel cultures in vitro. MSCs were seeded at high density ($10 \times 10^6$ cells/ml) in photocrosslinked gelatin hydrogel and cultured in osteogenic medium for 3 weeks. Cultures were harvested at 1, 2, and 3 week intervals, fixed, embedded, sectioned, and stained for mineralization using Alizarin Red. Robust mineralization is seen after 2 weeks of culture upon osteogenic stimulation, including intercellular matrix initially formed by the gelatin hydrogel scaffold. Mineralization is not seen in cMSCs cultured under control conditions.

Long bones from chick embryos at Day 17 of incubation were used to harvest bone marrow, which was then dissociated with collagenase, and the isolated cells plated in basal medium (DMEM+10% fetal bovine serum+antibiotics). After 2-3 days, non-attached cells were removed, and fresh medium added. The attached cells were seen to form proliferative colonies, and were allowed to reach 75% confluence, and then passaged by replating after 1:3 dilution. Morphology of the cells is shown in FIGS. 1A-1C.

Example 2

Ability of Isolated Chick Bone Marrow Mesenchymal Stem Cells (MSCs) to Undergo Induced Multilineage Differentiation In Vitro A principal hallmark of MSCs is their ability to undergo induced multi-lineage differentiation, specifically osteogenesis, chondrogenesis, and adipogenesis. The isolated chick MSCs were placed in standard differentiation media, and their differentiation monitored by histological staining after ~10 days. The chick MSCs were fully capable of undergoing osteogenic, chondrogenic, and adipogenic differentiation (FIGS. 2A-2D).

Example 3

Figure 5A:
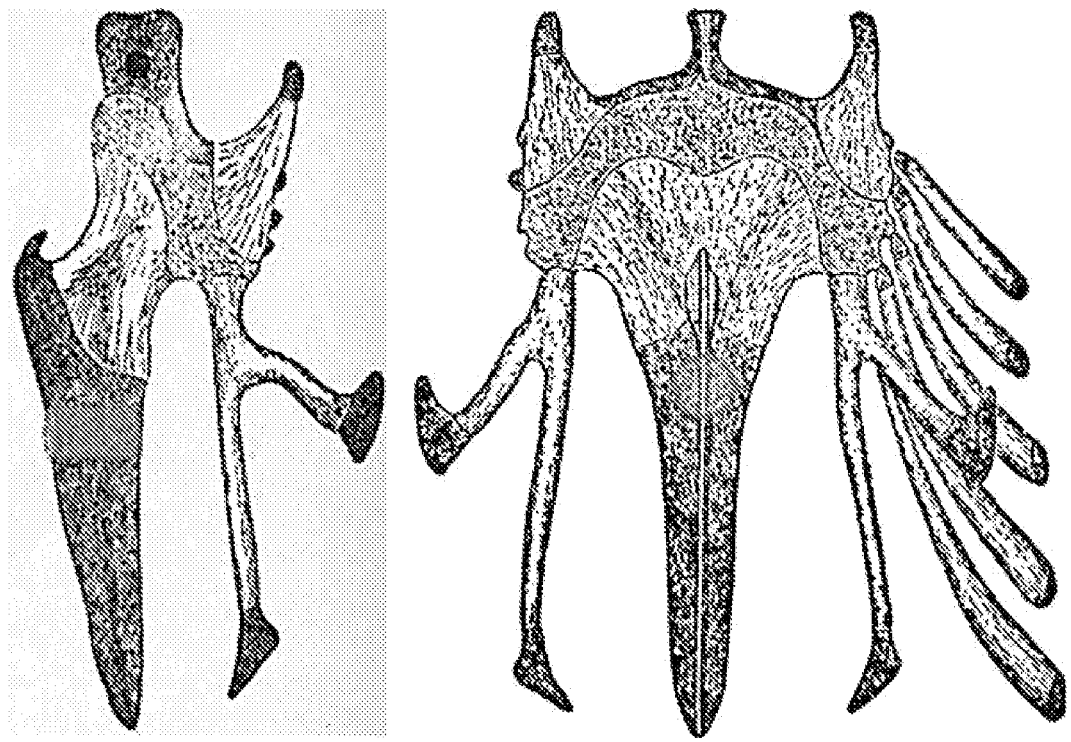
FIGS. 5A-5B. Structure of chick (A) sternum and (B) calvaria, and the site of surgical defect for MSC implantation.
Figure 5B:
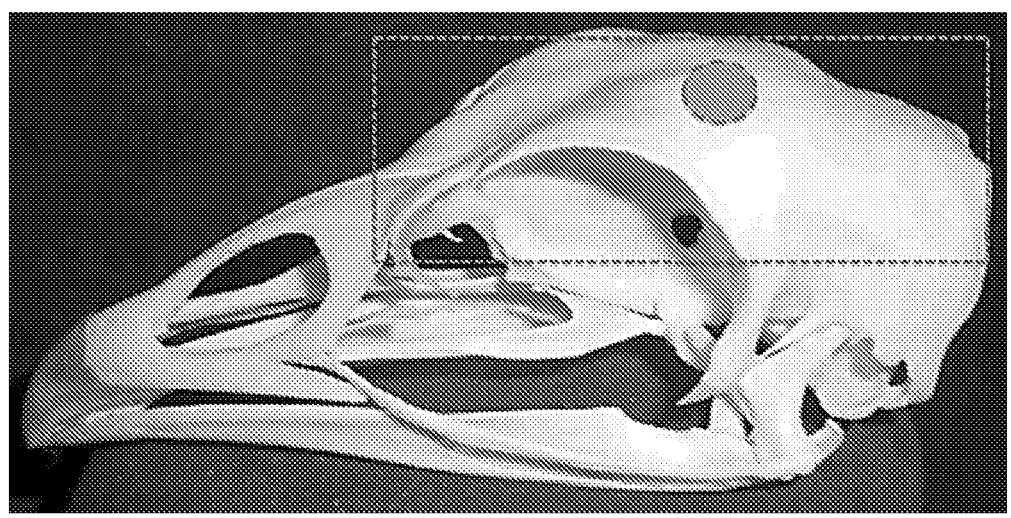
Figure 8A:
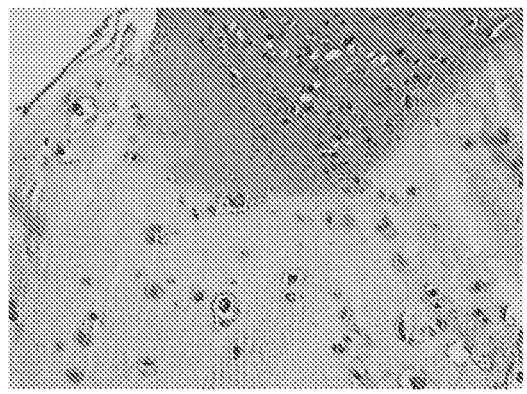
FIGS. 8A-8B. MSC-hydrogel constructs implanted into cartilage defect produce chondrocytes generating cartilage-specific matrix, consistent with reparative activity.
Figure 8B:
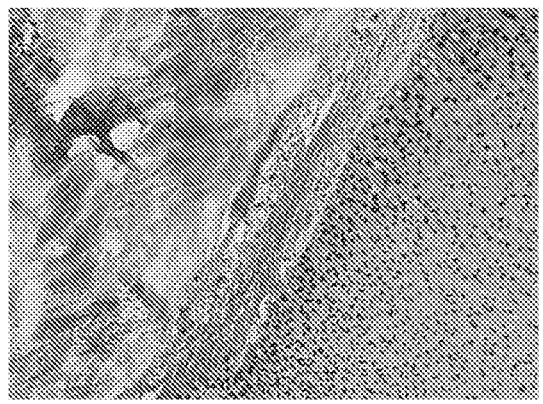
Figure 9A:
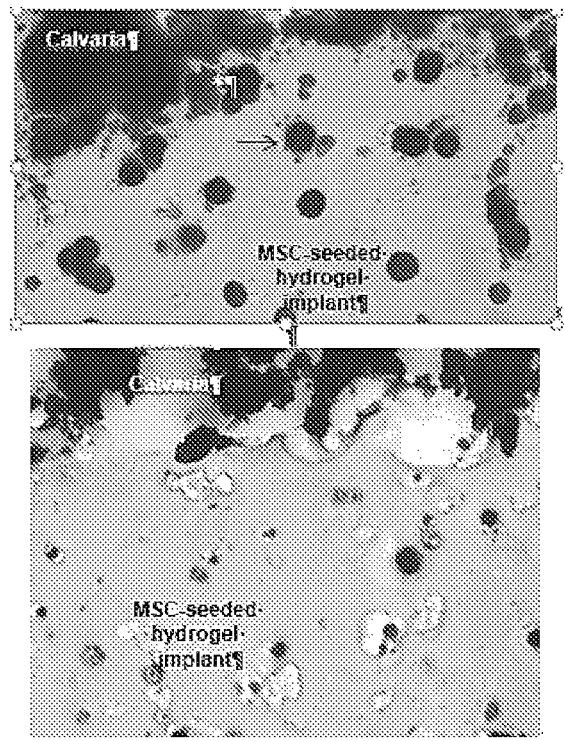
FIGS. 9A-9B. MSC-hydrogel implant into calvarial defect produce osteoblasts generating mineralized matrix, characteristic of bone tissue and consistent with reparative activity.
Figure 9B:
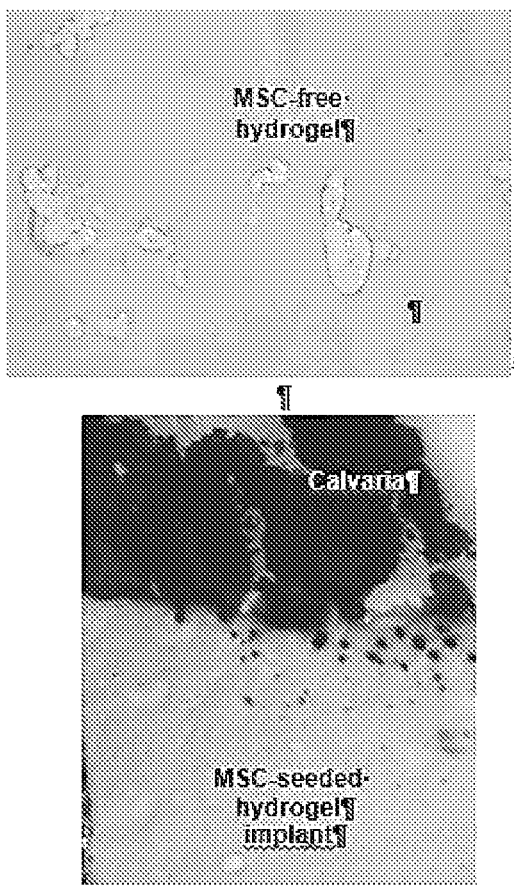
Figure 10:
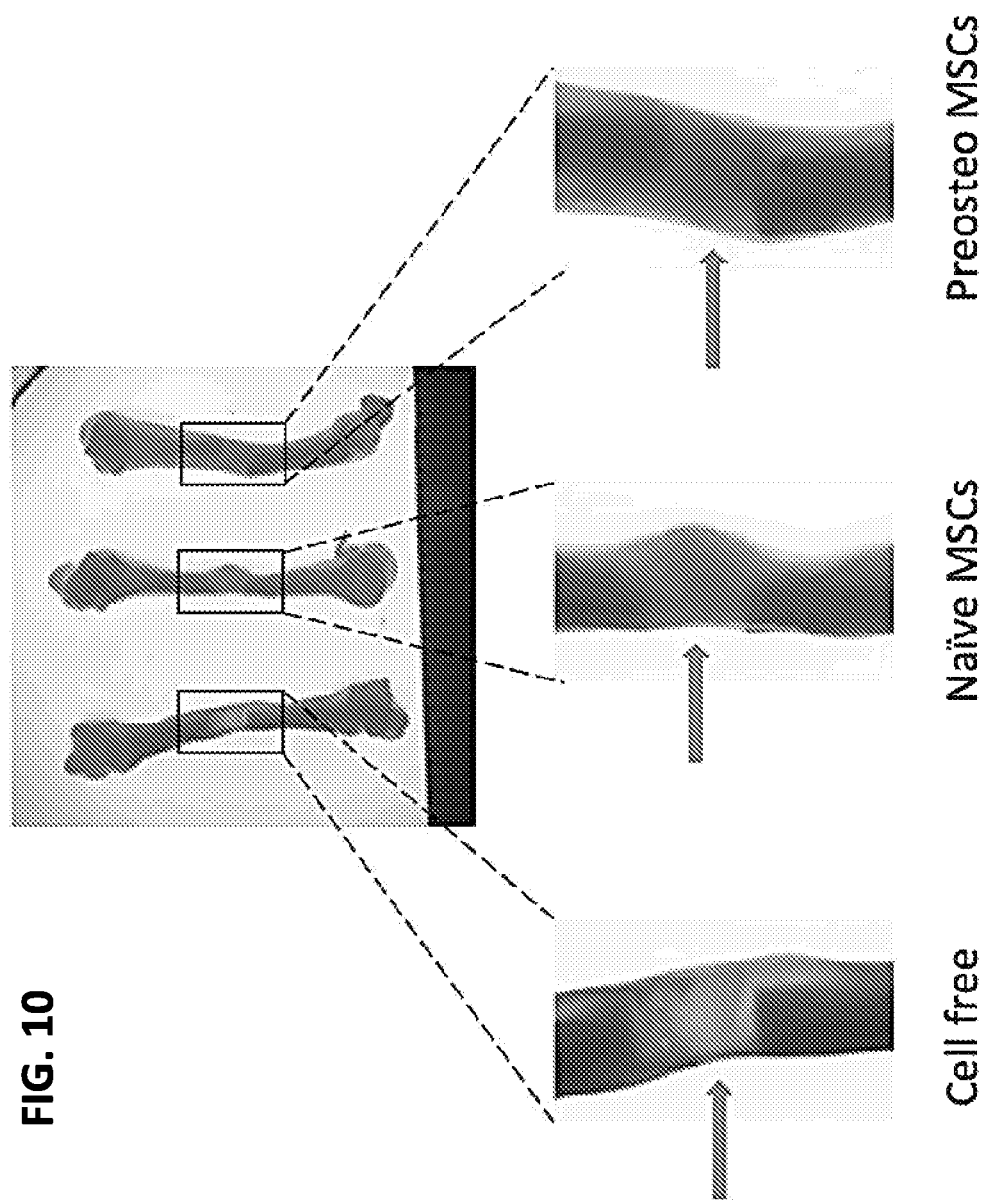

Demonstration of the Ability of Chick Bone Marrow MSCs to Repair Bone and Cartilage Defects Using an In Vitro Tissue Explant Model (A) Experimental Models
Cartilage:
The sternum was harvested from Day 17 chick embryos (FIG. 5A), and a 3 mm diameter circular defect was created in the mid-section of the tissue with a punch, and filled with chick MSCs encapsulated in a photocrosslinked gelatin hydrogel (see below). The composite construct was cultured for 3 weeks in a serum-free chondroinductive medium containing 10 ng/ml TGF-β1.
Bone:
The calvaria was harvested from Day 17 chick embryos (FIG. 5B), and a 3 mm diameter circular defect was created in the mid-section of the tissue with a punch, and filled with chick MSCs in a photocrosslinked gelatin hydrogel (see below). The composite construct was cultured for 3 weeks in an osteoinductive medium containing beta-glycerophosphate and ascorbate. Another example of ex vivo fracture repair was a critical sized defect in a long bone (Day 15 chick embryonic tibia), created surgically as a 2 mm gap. The defect was filled with chick MSCs encapsulated in a photocrosslinked gelatin hydrogel (see below). The composite construct was cultured similarly as the calvaria.
Delivery of MSCs in a Photocrosslinked Scaffold:
MSCs were mixed at $20\times10^6$ cells/ml in a visible light photocrosslinkable hydrogel as described (Un et al., 2013). The cell-gelation suspension was either first photocrosslinked then punched into appropriate plugs, or directly applied to the defect site, followed by illumination with visible light. Control consisted of delivery of photocrosslinked gelatin alone (i.e., MSC-free).
(B) Results
Cartilage Repair:
After 3-weeks of culture of the MSC-hydrogel/sternum composite, the cell-loaded hydrogel demonstrated obvious signs of cartilage formation, stained red with Safranin O, similar to the original host cartilage (FIG. 8A). While the initial cell density tested, $20\times10^6$ MSCs/ml, appeared to be too low for extensive, complete cartilage regeneration, the robust Safranin O-positive pericellular matrix and the apparent integration between host and implant matrices indicate that cartilage can be repaired. The reparative activity of the procedure can be optimized by increasing MSC seeding densities.
Bone Repair:
As shown in the histological staining of non-decalcified tissue sections (FIGS. 10A-10B), the calvaria/MSC-hydrogel constructs showed robust mineralization in the implant region, with the osteogenically differentiated MSCs demonstrating comparable mineralization level as in the calvaria tissue. H&E staining clearly indicates the cellular origin of the calcified matrix. While the seeding density is most likely lower than optimal for complete tissue repair, this can be optimized in future studies. In the long bone (tibia) defect repair, (FIGS. 10 and 11), macroscopic view showed substantial opacity in the MSC seeded cultures (FIG. 10), while histological examination revealed abundant cells in the MSC-seeded implanted constructs, which immunostained positively for a bone matrix protein, osteocalcin (FIG. 11).

Example 4

Figure 6:
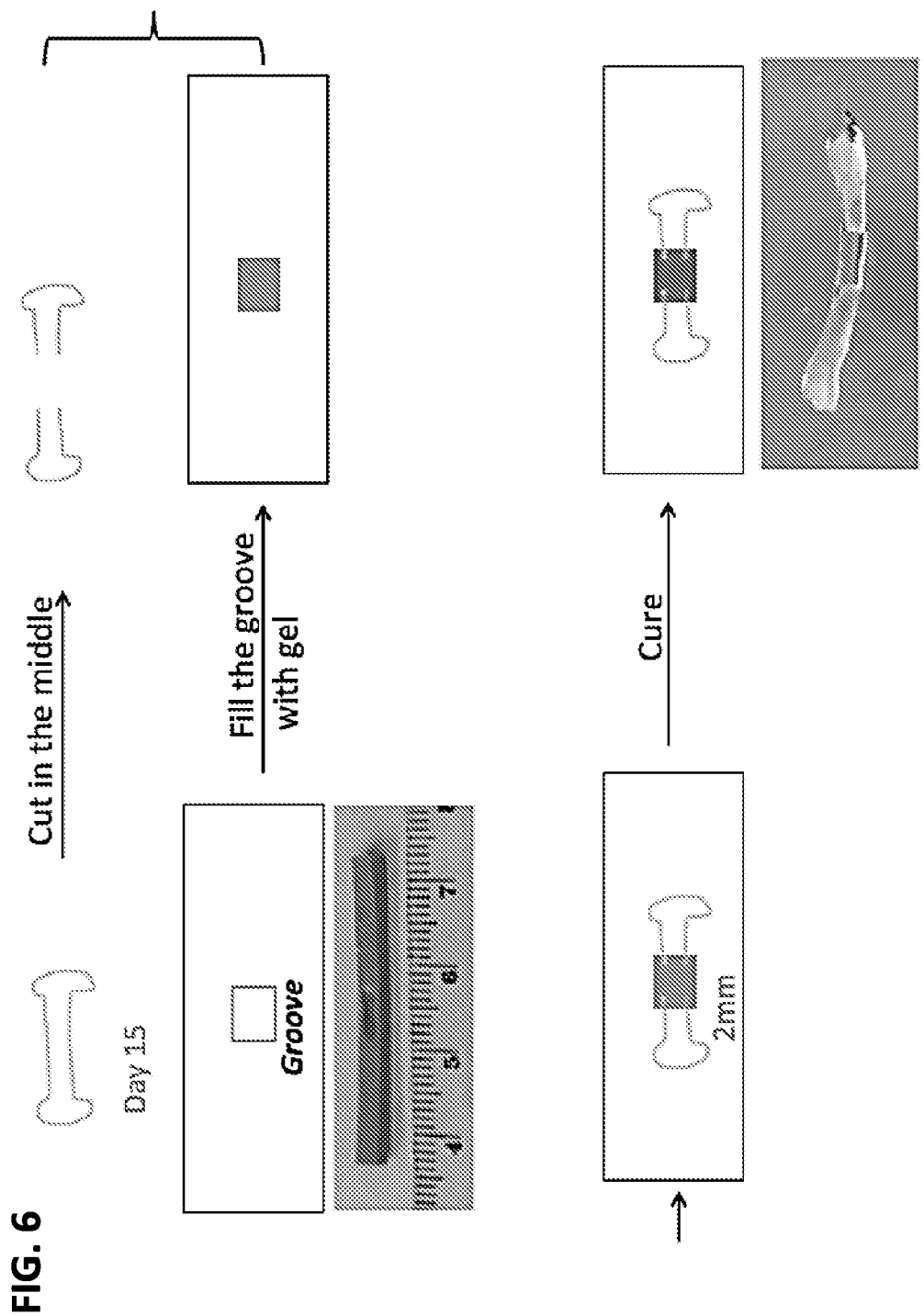
FIG. 6. An ex vivo model of avian long bone fracture repair. Incubation day 15 chick embryonic long bone (tibia) was used to create a 2 mm mid-diaphysis defect. The fractured bone was placed into a custom-designed culture plate insert with the defect lined up with a 5 mm groove in the insert. MSCs ($10 \times 10^6$ cells/ml) were placed into the defect/groove in photocrosslinkable gelatin, which was then photocured. The composite was incubated for up to 3 weeks.
Figure 7:
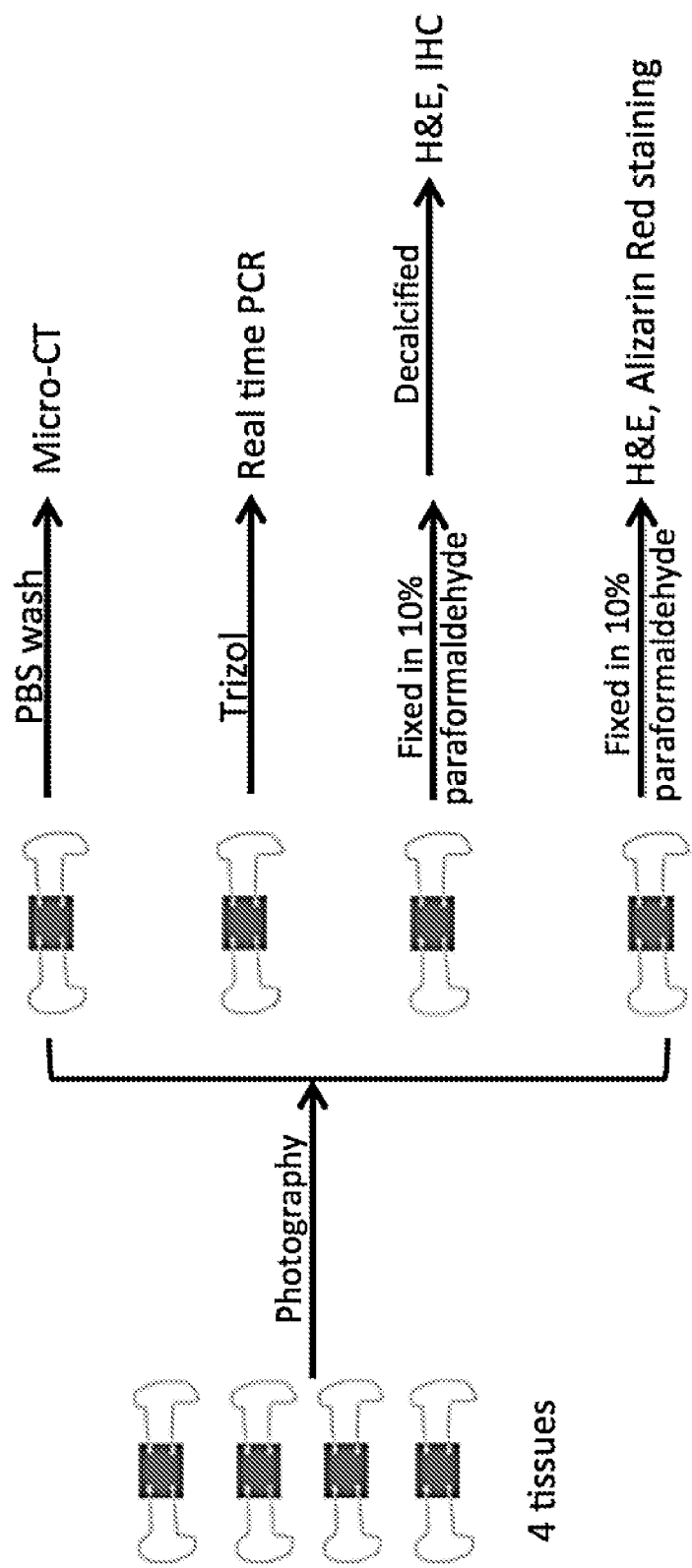
FIG. 7. Experimental groups and analyses in the ex vivo bone fracture repair experiment. Three groups of tibial explants were tested: (1) cell-free construct; (2) seeded with naïve MSCs; and (3) seeded with pre-osteogenically differentiated (2 weeks) MSCs. Tissues were harvested after up to 4 weeks and examined for mineralization (microCT and histology), and for osteogenesis-associated gene expression by RT-PCR.
Figure 12A:
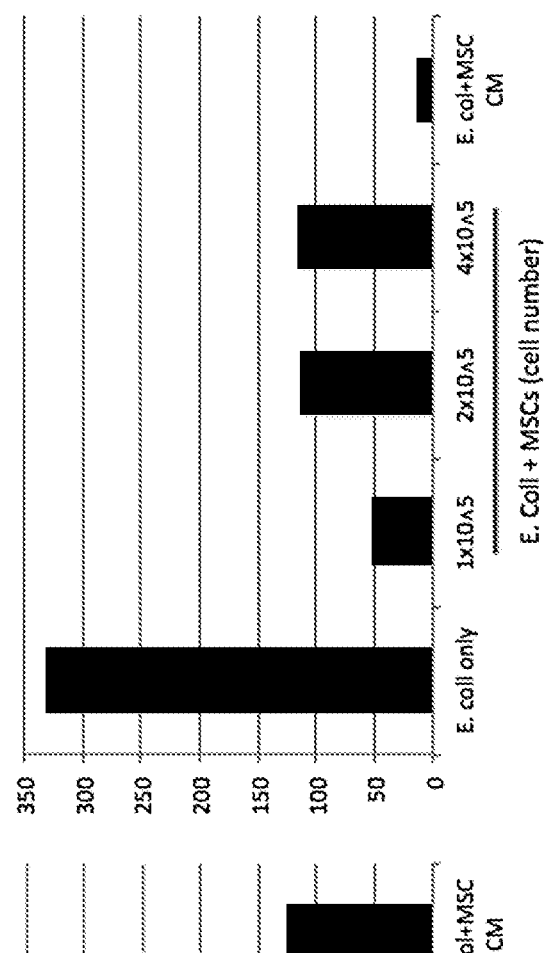
FIGS. 12A-12C. Anti-bacterial effects of bone marrow derived MSCs. *E. coli* were inoculated into culture medium containing (*E. coli*+MSCs) or conditioned by (CM) MSCs, incubated for 4 hours, and the medium was then sampled for bacteria concentration. Chick bone marrow-derived MSCs (FIG. 12A) demonstrate significant anti-bacterial effects, comparable to that of human bone marrow-derived MSCs (FIG. 12B). In comparison, bacteria sensitivity to a standard antibiotic, Ampicillin, is shown in (FIG. 12C).
Figure 12B:
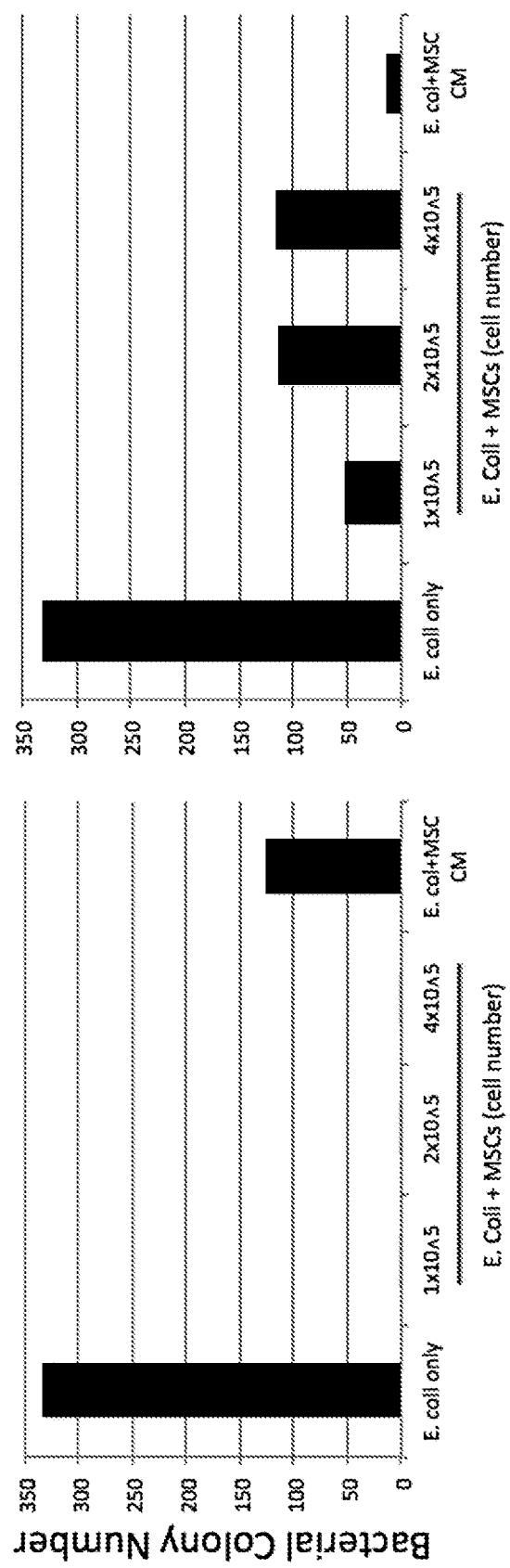
Figure 12C:
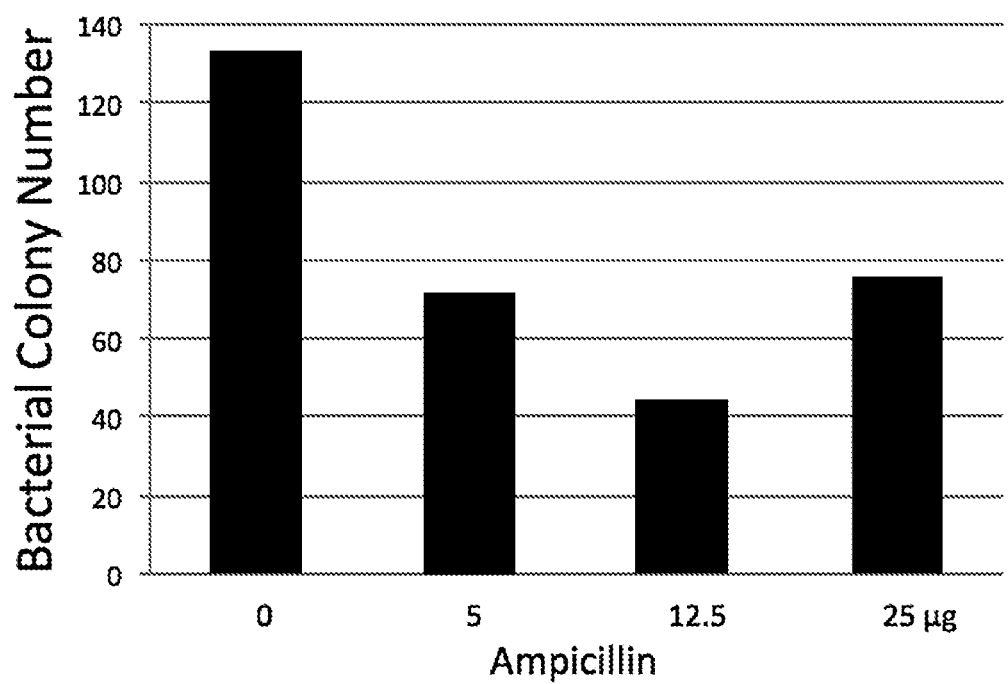

Demonstration of the Ability of MSCs to Suppress Bacterial Growth (A) Experimental Model
*Escherichia coli* (~$1\times10^4$ CFU) were inoculated into cultures of chick MSCs that were seeded in multi-well plates 24 hours at various seeding densities ($1\times10^5$ cells/ml, $2\times10^5$ cells/ml, and $4\times10^5$ cells/ml) and maintained in antibiotics-free medium, and then incubated for an additional 4 hours. Controls consisted of seeding into only medium previously conditioned for 24 hours by MSCs (chick or human), or control culture medium that had not been exposed to cells. Viable bacterial titers were determined at the end of the 4-hour incubation based on plating and standard colony counts. Treatment with a standard antibiotic, Ampicillin, was used as a positive control.
(B) Results
As shown in FIG. 6, exposure to either chick MSCs (FIG. 12A) or human MSCs (FIG. 12B) showed a significant suppression of bacterial growth; exposure to CM (medium conditioned by MSCs) was also effective. In comparison, as a positive control, treatment with the antibiotic, Ampicillin, resulted in an expected anti-bacterial effect (FIG. 12C). The results of this study demonstrated that MSCs are effective in reducing bacterial growth when added to *E. coli* cultures alone. This confirmed the antimicrobial activity of human MSCs (Krasnodembskaya et al., Stem cells. 2010; 28(12): 2229-38) and documented that avian MSCs possess similar bactericidal activity.

In view of the many possible embodiments to which the principles of the disclosed invention may be applied, it should be recognized that the illustrated embodiments are only preferred examples of the invention and should not be taken as limiting the scope of the invention. Rather, the scope of the invention is defined by the following claims. We therefore claim as our invention all that comes within the scope and spirit of these claims.

We claim:
1. A method for forming bone and/or cartilage in an avian subject with a bone defect, comprising:
   administering locally to the bone defect in the avian subject a therapeutically effective amount of a composition comprising avian mesenchymal stem cells and a hydrogel that supports the differentiation of the avian mesenchymal stem cells into cells of an osteogenic and/or chondrogenic lineage, wherein the hydrogel is a methacrylated gelatin hydrogel or methacrylated hyaluronan hydrogel, or a mixture thereof; and
   photocrosslinking the hydrogel with visible light,
   thereby forming bone and/or cartilage and treating the bone defect in the avian subject.
2. The method of claim 1, wherein the hydrogel is biodegradable.
3. The method of claim 1, wherein the hydrogel comprises methacrylated gelatin.
4. The method of claim 1, further comprising administering to the avian subject at least one agent that induces or accelerates the differentiation of the mesenchymal stem cells into the osteogenic lineage.

5. The method of claim 1, wherein the avian subject has a fracture, and avian mesenchymal stem cells and the hydrogel are delivered to the fracture.

6. The method of claim 5, wherein the fracture is a result of trauma.

7. The method of claim 5, wherein the fracture is result of an underlying physiological condition.

8. The method of claim 5, wherein the underlying physiological condition is osteogenesis imperfecta or a metabolic bone disease.

9. The method of claim 1, wherein the avian subject is a bird of the order Anseriformes, Apodiformes, Caprimulgiformes, Charadriiformes, Ciconiformes, Columbiformes, Coraciiformes, Falconiformes, Galliformes, Gaviidae, Passeriformes, Pelicaniformes, Phoenicopteriformes, Piciformes, Podicipediformes, Psittqciformes, or Strigidae.

10. The method of claim 1, wherein the avian subject is an exo bird, a chicken, a pigeon, or a bird of prey.

11. The method of claim 1, wherein the avian subject is a member of the family of Accipitridae, Pandionidae, Sagittariidae, Falconidae, Cathartidae, Strigidae or Tyonidae.

12. The method of claim 1, wherein the avian subject is an owl, falcon or hawk.

13. The method of claim 1, wherein the avian subject is a chicken.

14. The method of claim 1, wherein the avian subject is a falcon.

15. A method of repairing an infected hone defect in an avian subject, comprising:

administering locally to the bone defect a therapeutically effective amount of a composition comprising avian mesenchymal stern cells and a hydrogel, wherein the hydrogel is a methacrylated gelatin hydrogel or methacrylated hyaluronan hydrogel, or a mixture thereof; and photocrosslinking the hydrogel with visible light, thereby repairing the bone defect and treating the infection in the avian subject, wherein the infection is a *Staphylococcus* infection, an *Escherichia coli* infection, or an *Enterococcus* species infection.

16. The method of claim 15, wherein the hydrogel is the methacrylated gelatin hydrogel.

17. The method of claim 15, wherein the hydrogel is the methacrylated hyaluronan hydrogel.

18. The method of claim 15, further comprising administering to the avian subject at least one agent that induces or accelerates the differentiation of the mesenchymal stem cells into the osteogenic lineage.

19. The method of claim 15, wherein the avian subject is a bird of the order Anseriformes, Apodiformes, Caprimulgiformes, Charadriiformes, Ciconiformes, Columbiformes, Coraciiformes, Falconiformes, Galliformes, Gaviidae, Passeriformes, Pelicaniformes, Phoenicopteriformes, Piciformes, Podicipediformes, Psittqciformes, or Strigidae.

20. The method of claim 15, wherein the avian subject is an exotic bird, a chicken, a pigeon, or a bird of prey.

21. The method of claim 15, wherein the avian subject is a member of the family of Accipitridae, Pandionidae, Sagittariidae, Falconidae, Cathartidae, Strigidae or Tyonidae.

* * * * *

UNITED STATES PATENT AND TRADEMARK OFFICE
CERTIFICATE OF CORRECTION

PATENT NO.        : 10,864,234 B2
APPLICATION NO.   : 15/525570
DATED             : December 15, 2020
INVENTOR(S)       : Tuan Page 1 of 1

It is certified that error appears in the above-identified patent and that said Letters Patent is hereby corrected as shown below:

In the Claims

Column 29, Claim 15, beginning at Line 28, "A method of repairing an infected hone defect in an avian subject, comprising:" should read -- A method of repairing an infected bone defect in an avian subject, comprising: --.

Signed and Sealed this
Fifteenth Day of June, 2021

Drew Hirshfeld
*Performing the Functions and Duties of the
Under Secretary of Commerce for Intellectual Property and
Director of the United States Patent and Trademark Office*